US007943314B2

(12) United States Patent
Wilson et al.

(10) Patent No.: US 7,943,314 B2
(45) Date of Patent: May 17, 2011

(54) METHODS OF DETECTING VIABILITY-ASSOCIATED MOLECULES

(75) Inventors: Stuart Wilson, Upper Norwood (GB); Sharon Banin, Finchley (GB)

(73) Assignee: ISEAO Technologies Limited, London (GB)

( * ) Notice: Subject to any disclaimer, the term of this patent is extended or adjusted under 35 U.S.C. 154(b) by 166 days.

(21) Appl. No.: 11/993,986

(22) PCT Filed: Jul. 3, 2006

(86) PCT No.: PCT/GB2006/002475
§ 371 (c)(1),
(2), (4) Date: Dec. 19, 2008

(87) PCT Pub. No.: WO2007/003938
PCT Pub. Date: Jan. 11, 2007

(65) Prior Publication Data

US 2009/0215047 A1 Aug. 27, 2009

(30) Foreign Application Priority Data

Jul. 1, 2005 (GB) .................................. 0513535.5

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ..... 435/6; 536/23.1, 536/24.3
See application file for complete search history.

(56) References Cited

U.S. PATENT DOCUMENTS

| | | | | |
|---|---|---|---|---|
| 4,303,752 | A * | 12/1981 | Kolehmainen et al. | 435/8 |
| 5,766,868 | A | 6/1998 | Seto | |
| 7,083,911 | B2 * | 8/2006 | Wood et al. | 435/4 |
| 7,241,584 | B2 * | 7/2007 | Wood et al. | 435/8 |
| 7,422,868 | B2 * | 9/2008 | Fan et al. | 435/29 |
| 2002/0028208 | A1 * | 3/2002 | Collisson et al. | 424/188.1 |
| 2002/0115140 | A1 * | 8/2002 | Levinson et al. | 435/69.1 |
| 2003/0003540 | A1 | 1/2003 | Young et al. | |
| 2003/0036092 | A1 * | 2/2003 | Iverson et al. | 435/7.1 |
| 2004/0142401 | A1 | 7/2004 | Iwata et al. | |
| 2005/0048592 | A1 | 3/2005 | Wood et al. | |
| 2008/0113040 | A1 * | 5/2008 | Doona et al. | 424/661 |
| 2009/0081644 | A1 * | 3/2009 | Nelson et al. | 435/6 |

FOREIGN PATENT DOCUMENTS

| | | | |
|---|---|---|---|
| EP | 1 211 322 | * | 6/2002 |
| EP | 1321763 | | 6/2003 |
| WO | 9511996 | | 5/1994 |
| WO | 9531570 | | 11/1995 |
| WO | WO00/18953 | * | 4/2000 |
| WO | WO00/49171 | * | 8/2000 |
| WO | 02066671 | | 8/2002 |
| WO | 02088394 | | 11/2002 |
| WO | 2004106547 | | 12/2004 |
| WO | 2005003386 | | 1/2005 |

OTHER PUBLICATIONS

Bac-Titer-Glo Microbial Cell Viability Asssay : Promega Technical Bulletin No. 337 (Apr. 2004).*

Cell-Titer-Glo Luminescent Cell Viability Asssay : Promega Technical Bulletin No. 288 (Feb. 2004).*

Lauer et al., Cloning, nucleotide sequence, and engineered expression of Thermus thermophilus DNA ligase, a homolog of *Escherichia coli* DNA ligase. Journal of Bacteriology 173 (16) : 5047-6053 (1991).*

Panasenko et al., A simple, three-step procedure for the large scale purification of DNA ligase from a hybrid lambda lysogen constructed in vitro. Journal of Biological Chemistry 253(13) : 4590-4592 (1978).*

Thore et al., Detection of Bacteriuria by Luciferase Assay of Adenosine Triphosphate. J. of Clinical Microbiology 1(1) : 1-8 (1975).*

Buimer, M. et al, Detection of *Chlamydia trachomatis* and *Neisseria gonorrhoeae* by Ligase Chain Reaction-Based Assays with Clinical Specimens from Various Sites; Implacation of Diagnostic Testing and Screening; Journal of Clinical Microbiology; Oct. 1996; pp. 2395-2400; vol. 34, No. 10.

Cao, Weiguo, Recent developments in ligase-mediated amplification and detection; Trends in Biotechnology; Jan. 2004, pp. 38-44; vol. 22, No. 1.

Keer, J.T. and Birch, J.; Molecular methods for the assessment of bacterial viability; Journal of Microbiological Methods 53; 2003; pp. 175-183. Search Report under Section 17 for GB 0513535.5 dated Oct. 18, 2005.

International Search Report for PCT/GB2006/002475, mailed Jun. 22, 2007.

Buimer et al., "Detection of *Chlamydia trachomatis* and *Neisseria gonorrhoeae* by Ligase Chain Reaction-Based Assyas with Clinical Specimens from Various Sites: Implications for Diagnostic Testing and Screening", Journal of Clinical Microbiology, Oct. 1996, 34(10):2395-2400.

International Preliminary Report on Patentability dated Jan. 9, 2008.

Communication pursuant to Article 94(3) EPC dated Jun. 2, 2008.

Annex to Communication pursuant to Article 94(3) EPC dated Jun. 2, 2008.

Response dated Oct. 10, 2008 to Communication pursuant to Article 94(3) EPC dated Jun. 2, 2008.

Claim Amendments accompanying Response dated Oct. 10, 2008.

Invitation pursuant to Article 94(3) and Rule 71(1) EPC dated Feb. 2, 2010.

Response dated Apr. 23, 2010 to Invitation pursuant to Article 94(3) and Rule 71(1) EPC dated Feb. 2, 2010.

Claim Amendments accompanying Response dated Apr. 23, 2010.

Amendments to Specification accompanying Response dated Apr. 23, 2010.

* cited by examiner

*Primary Examiner* — Ethan Whisenant

(74) *Attorney, Agent, or Firm* — Andrus, Sceales, Starke & Sawall, LLP

(57) ABSTRACT

A method of detecting a molecule associated with viability of one or more cells or organisms in a sample comprises the initial step of contacting the sample with an enzyme, which enzyme is capable of adding or removing a chemical moiety to or from a nucleic acid molecule in the presence of the molecule associated with viability of the of the one or more cells or organisms. This thereby generates a novel detectable nucleic acid molecule. The next step involves detecting the presence of the molecule associated with viability of the one or more cells or organisms by detecting the novel nucleic acid molecule generated only in the presence of the molecule associated with viability of the one or more cells or organisms. A most preferred molecule associated with viability is ATP, although NAD may also be detected. A preferred enzyme for use in the methods is ligase. The method has numerous applications, in particular in monitoring viability of cells, toxicology testing and determining whether there is contamination in a sample or on a surface. Kits are also provided for carrying out the methods.

19 Claims, 4 Drawing Sheets

METHODS OF DETECTING VIABILITY-ASSOCIATED MOLECULES

FIELD OF THE INVENTION

The present invention relates to the field of detecting molecules associated with viability of a cell or organism, for example in microbe detection. More particularly, the present invention relates to methods of detecting cells or organisms which are considered to be contaminants in a sample. The methods of the invention are highly sensitive and overcome the problems of prior art methods.

BACKGROUND TO THE INVENTION

Measuring the presence and levels of certain molecules which are associated with cell viability is important in a number of contexts. For example, measuring levels of ATP is useful in mammalian cells for growth analysis and toxicology purposes.

Such molecules can also act as a useful marker in hygiene applications. Detection of the contaminating molecule on a surface indicates that the surface has not been cleaned or requires cleaning to the required standard.

Contamination of various products for human consumption and use by organisms such as bacteria and yeast and by cells of plant or animal origin represents an important consideration in terms of both safety and economics in a wide range of fields.

For example, water supplies, wastewater, marine environments, pharmaceutical products, cosmetic products, food, beverages, clinical samples including blood and platelet samples etc are all regularly tested for contamination by potentially harmful organisms and cells. Often, the organisms include bacterial species.

In many cases, tests are carried out based upon measuring the presence of a molecule which can be linked to the presence in the sample of a contaminant cell or organism. The most commonly detected molecule is Adenosine Triphosphate (ATP).

A routinely employed method for determining ATP levels involves the use of bioluminescence. The method uses the ATP dependency of the reaction in which light emitting luciferase catalyzes oxidation of luciferin. The method may be used to measure relatively low concentrations of ATP. Kits useful for detecting ATP using bioluminescence are commercially available from Roche, New Horizons Diagnostics Corp, Celsis etc.

A number of problems exist with respect to bioluminescence detection. For example, detection of microbial ATP only, in the presence of ATP from non-microbial sources can be a problem. This problem has been solved to a certain degree by use of filters which can separate bacteria from non-bacterial sources of ATP, thus providing a more accurate signal.

In addition, chemicals and/or metals in a sample can interfere with the bioluminescence reaction. This is of particular relevance, for example, where surface contamination is being measured following cleaning of a surface using cleaning agents. The chemical cleaning agents interfere with the luciferase catalysed reaction, and thus in some cases lead to false negative results, where microbial or other contaminant ATP is present but the bioluminescence reaction is not effective.

Ligases are well known enzymes which catalyze ligation of the 5' end of a nucleic acid molecule to the 3' end of a further nucleic acid molecule. The ligation reaction requires ATP in order to activate the enzyme. Ligases are commercially available and are supplied pre-loaded with an AMP molecule which allows them to catalyze ligation without activation by an ATP molecule.

DESCRIPTION OF THE INVENTION

The present invention provides improved methods and kits for detecting contamination in a sample caused by organisms such as bacteria and yeast or cells of any origin, such as mammalian, other animal or plant origin. The methods and kits are also useful in other applications where determination of levels of a molecule associated with viability is useful.

Accordingly, in a first aspect, the invention provides a method of detecting a molecule associated with viability of one or more cells or organisms in a sample, comprising, consisting essentially of or consisting of the steps of:

a) contacting the sample with an enzyme, which enzyme is capable of adding or removing a chemical moiety to or from a nucleic acid molecule in the presence of the molecule associated with viability of the one or more cells or organisms, thereby generating a novel detectable nucleic acid molecule; and
b) detecting the presence of the molecule associated with viability of the one or more cells or organisms by detecting the novel nucleic acid molecule generated only in the presence of the molecule associated with viability of the one or more cells or organisms.

Preferably, the molecule associated with viability is required to activate the enzyme to a form in which it is capable of acting on the nucleic acid molecule.

Thus, by detecting sensitively the molecule associated with viability, the presence of cells of any source may be detected in a sample. In some embodiments of the invention it may be desirable to test for the presence of viable cells, for example in toxicity and compound screening tests. In other embodiments, the presence of a molecule associated with viability may be utilised in order to determine the presence of some form of contamination of the sample. The methods of the invention may usefully be used to quantify levels of the molecule associated with viability, in particular to determine levels of ATP and/or $NAD^+$. This may be useful for example in methods of monitoring growth of a particular cell culture.

Therefore, there is provided a method of detecting one or more viable cells or organisms in a sample, comprising the steps of:

(a) contacting the sample with an enzyme, which enzyme is capable of adding or removing a chemical moiety to or from a nucleic acid molecule in the presence of a molecule associated with viability of the one or more cells or organisms, thereby generating a novel detectable nucleic acid molecule; and
(b) detecting the presence of the viable one or more cells or organisms by detecting the novel nucleic acid molecule generated only in the presence of the molecule associated with viability of the one or more cells or organisms.

The one or more cells or organisms means one or more types, species, strains etc of cell or organism rather than the actual number of each cell or organism in the sample. The methods of the invention provide improved sensitivity of detection as compared to prior art methods and can detect extremely low numbers of molecules derived from cells or organisms in the sample. The term "organism" includes within its scope micro-organisms such as bacteria and yeast. The cells may be of any type in which cell viability is of interest. For example, mammalian cell viability may be usefully measured for determining toxicology of a candidate pharmaceutical agent. Molecules associated with viability which are detected on a surface may indicate contamination of that surface and may be of any origin, for example of plant or animal origin.

The method relies on the fact that if there are one or more cells or organisms present in the sample, the molecule associated with viability will be present. This molecule activates the enzyme present in the sample and thus allows the enzyme to catalyse a reaction in which a chemical moiety is added to the nucleic acid molecule or a chemical moiety is removed from the nucleic acid molecule. This moiety addition or removal generates a novel detectable nucleic acid molecule (in a subsequent process). In one embodiment, the moiety addition or removal confers the nucleic acid molecule with the ability to be extended, for example by polymerisation or ligation to a further nucleic acid molecule, to thus generate a novel detectable nucleic acid molecule. The novel nucleic acid molecule may be detected, thereby allowing a determination of the presence of the molecule associated with viability of the one or more cells or organisms in the sample under test.

Thus, if the one or more cells or organisms is/are not present in the sample, there will be no molecule associated with viability of the one or more cells or organisms and so the chemical moiety will not be added or removed and thus the novel detectable nucleic acid molecule will not be generated.

The term "molecule associated with viability" includes within its scope any molecule which can act as an indicator of the viability of the one or more cells or organisms which are being detected in the sample. The molecule associated with viability interacts with the enzyme and thus, in the presence of the molecule, the enzyme is able to act on the nucleic acid molecule, leading to the generation of a novel detectable nucleic acid molecule. The molecule associated with viability of the one or more cells or organisms may activate the enzyme, thus allowing it to perform its catalytic function for example. In a most preferred embodiment, the molecule associated with viability comprises, consists essentially of, or consists of ATP. ATP is the standard molecule used to indicate the presence of a contamination in a sample, such as a microbial contamination, and also may usefully be used in toxicology assays and monitoring cell culture growth, for example.

Any source of ATP may be included within the scope of the invention. For example, ATP may be generated from $ATP_4$ for example or by the reaction of AMP and PPi. ATP may be generated by a reaction catalysed by phosphotransferases such as Adenylate Kinase (ADK) for example (ADP+MgADP $\rightleftharpoons$ AMP+MgATP).

The term "chemical moiety" is well known in the art and includes by way of example and not limitation, phosphate groups, carbohydrate groups, nucleotides, nucleic acid molecules and acetyl groups etc. Any "chemical moiety" is included within the scope of the invention provided its addition or removal to or from a nucleic acid molecule may be catalysed by an enzyme in the presence of a molecule associate with viability of the one or more cells or organisms to thereby generate a novel detectable nucleic acid molecule.

The method is not limited to addition or removal of a single chemical moiety per nucleic acid molecule. The term "a chemical moiety" may, therefore, include multiple copies of the chemical moiety in question.

An "addition" of a chemical moiety may include, by way of example but not limitation, addition of nucleotides, nucleic acid molecules, acetyl or phosphate groups. Addition may be at the 5' or 3' end or at any point within the nucleic acid molecule.

A "removal" of a chemical moiety may include, but is not limited to, removal of nucleotides, nucleic acid molecules, acetyl and phosphate groups from terminal ends of the nucleic acid molecule or from anywhere along the nucleic acid molecule.

"Extended" is defined herein to include any increase in the length of the nucleic acid molecule when subjected to a further process as compared to the starting, unmodified (in terms of addition or removal of a chemical moiety) nucleic acid molecule. As stated, the extension leads to the generation of a novel detectable nucleic acid molecule.

Examples of "further processes" which may result in extension of the nucleic acid molecule to which the chemical moiety has been added or from which the chemical moiety has been removed include, by way of example and not limitation, ligation and polymerisation. The further process may occur consecutively or simultaneously with the addition or removal of the chemical moiety.

For the avoidance of doubt, it is hereby stated that the novel detectable nucleic acid molecule will have a different overall structure to that of the original nucleic acid molecule. Thus, the novel detectable nucleic acid molecule may contain additional nucleotides such that the novel nucleic acid molecule may be uniquely identified, for example by amplification utilising primers which can only bind and produce an amplification product using the novel nucleic acid molecule as a template. However, it may be that only one strand is extended as compared to the (original) nucleic acid molecule.

Many such additions or removals of chemical moieties which generate a novel detectable nucleic acid molecule and/or confer on the nucleic-acid molecule the ability to be extended (in a subsequent process) to generate a novel detectable nucleic acid molecule are well known in the art, but are not intended to be limiting with respect to the present invention. For example, the addition or removal of a chemical moiety to or from a nucleic acid molecule may comprise, consist essentially of or consist of ligation of the nucleic acid molecule with a further nucleic acid molecule, whereby the further nucleic acid molecule represents the "added" chemical moiety. Alternatively, for example, the addition or removal of a chemical moiety to or from a nucleic acid molecule may be catalysed by a suitable ATP dependent polymerase. Polymerisation generates the novel nucleic acid molecule which may then be detected.

The nucleic acid molecules for use in the methods, and inclusion in the kits, of the invention, must be of sequence and structure such that the enzyme in the sample may cause the addition or removal of a chemical moiety to or from the nucleic acid molecule in the presence of a molecule associated with viability of the one or more cells or organisms, thereby generating a novel nucleic acid molecule.

Suitable nucleic acid molecules for use in the invention are set forth as SEQ ID Nos 1 to 11 and described in more detail in the experimental section below.

"Nucleic acid" is defined herein to include any natural nucleic acid and natural or synthetic analogues that are capable of being modified by the addition or removal of a chemical moiety to or from a nucleic acid molecule which thereby generates a novel detectable nucleic acid molecule. Suitable nucleic acid molecules may be composed of, for example, double or single-stranded DNA and double or single-stranded RNA. Nucleic acid molecules which are partially double-stranded and partially single-stranded are also contemplated, and indeed are preferred in certain embodiments of the invention, provided the enzyme activity being investigated may add or remove a chemical moiety to or from the nucleic acid molecule. Most preferably the nucleic acid molecules will comprise dsDNA. The term "nucleic acid" encompasses synthetic analogues which are capable of being modified by an enzyme in a sample in an analogous manner to natural nucleic acids, for example nucleic acid analogues incorporating non-natural or derivatized bases, or nucleic acid analogues having a modified backbone. In particular, the term "double-stranded DNA" or "dsDNA" is to be interpreted as encompassing dsDNA containing non-natural bases. Similarly, "dsRNA" is to be interpreted as encompassing dsRNA containing non-natural bases.

A "sample" in the context of the present invention is defined to include any sample in which it is desirable to test for the presence of a particular molecule associated with viability of a cell(s) or organism(s). Thus the sample may comprise, consist essentially of or consist of a clinical sample, or an in vitro assay system for example. Samples may comprise, consist essentially of or consist of beverage or food samples or preparations thereof, or pharmaceutical or cosmetic products such as personal care products including shampoos, conditioners, moisturisers etc., all of which are tested for microbial contamination as a matter of routine. The sample may comprise, consist essentially of or consist of tissue or cells and may comprise, consist essentially of or consist of a sputum or a blood sample or a platelet sample for example. In addition, the methods and kits of the invention may be used to monitor contamination of surfaces, such as for example in locations where food is being prepared. Contamination is indicated by the presence of a molecule associated with viability. The contamination may be of any source, for example microbial, plant or animal contamination. Furthermore, the invention is also useful in monitoring environmental conditions such as water supplies, wastewater, marine environments etc. The invention is also useful in monitoring bacterial growth in fermentation procedures and in air sampling where bacteria or spore content can be assessed in hospital, industrial facilities or in biodefence applications. In a toxicology application, the sample may comprise, consist essentially of or consist of cells, preferably mammalian or plant cells. The cells may be contacted with a test agent and the viability of the cells following exposure to the agent determined using the methods of the invention.

"Diagnosis" is defined herein to include monitoring the state and progression of the disease, checking for recurrence of disease following treatment and monitoring the success of a particular treatment. The tests may also have prognostic value, and this is included within the definition of the term "diagnosis". The tests may have value in the clinic to detect early microbial infections, when levels of the one or more organisms are still low and before symptoms have been presented in the subject.

The terms "comprises" and "having" are defined herein to be not limiting in terms of the elements referred to and should be accorded the meaning "includes" or equivalent. "Consisting essentially of" is defined to allow for the presence of additional elements provided that the basic, novel characteristics of the elements recited are not changed by the presence of the additional elements.

Advantages Of The Invention

The method of the present invention provides significant technical advantages, due in large part to the fact that a novel nucleic acid molecule is generated as part of the method. This novel nucleic acid molecule provides a stable positive signal to indicate the presence of the one or more organisms in the sample, as compared to light production in bioluminescence detection which rapidly diminishes.

Furthermore, the novel nucleic acid molecule which is generated in the presence of the molecule associated with viability in the sample may be amplified for example which provides for increased sensitivity of detection of the molecule associated with viability in the sample. Detection of the molecule associated with viability in the sample may be carried out down to picomolar levels and below. Nucleic acid amplification techniques, such as TMA or PCR are robust and the product can be detected by commercially available and reliable instrumentation.

In addition, ligases are more stable than luciferase, which has previously been used in determining contamination, for example by micro organisms, in samples. Thus, cleaning agents, such as trichloroacetic acid and sodium hypochlorite (bleach) which are commonly used on surfaces which are then screened for any residual contamination inhibit luciferase activity in a potent manner. This can give rise to false negative signals, meaning that a contamination is still present on the surface but is not detected because the assay is no longer effective. These false signals are removed by the methods and kits of the invention.

Additionally, the methods of the invention have applicability to large volumes; for example where the enzyme (which may be a ligase for example) is immobilised, a molecule associated with viability such as ATP, may be detected from a large volume of fluid, thereby enhancing sensitivity over existing methods. For example, 1 to 5 ml, or in the case of water testing a larger volume such as 100 ml of sample may be used with an immobilised ligase column and all the ATP released from bacterial cells in this volume can be accessed.

A further advantage of the invention is that the immobilised enzyme may be washed to remove inhibitory materials that could affect the subsequent detection process. This is possible because the enzyme-viability marker link or bond, preferably an ATP-ligase link, is stable during the washing process. This is a major advantage over the existing ATP bioluminescence techniques which are very susceptible to inhibitors (as discussed above).

Furthermore, the methods of the invention do not rely upon standard techniques such as growing up cultures and plating etc, which means the methods of the invention are much quicker and easier to perform.

Preferred Embodiments

In a most preferred embodiment of the invention, the novel nucleic acid molecule is generated by ligation of the nucleic acid molecule with one or more further nucleic acid molecules. The nucleic acid molecule and further nucleic acid molecule(s) may be any suitable nucleic acid molecules which may be ligated to form a novel nucleic acid molecule. Preferably, the nucleic acid molecule and further nucleic acid molecule(s) are designed such that they do not have high levels of homology with the genome of the one or more cells or organisms which produce the molecule associated with viability which is to be detected in the sample. This means that, even in the presence of contaminating nucleic acid molecules, only the novel nucleic acid molecule may be detected.

Preferably, the homology is less than about 5%, less than about 10%, less than about 12.5%, less than about 15%, less than about 20%, less than about 30%, less than about 40% sequence identity with the corresponding nucleotide sequence from the one or more cells or organisms which produce the molecule associated with viability which is to be detected in the sample. In one embodiment, there is no sequence identity with the corresponding nucleotide sequence from the one or more cells or organisms over approximately 10, 20, 30, 40 or 50 contiguous nucleotides. In another embodiment, there is less than about 10% or less than about 12.5% sequence identity over approximately 10, 20, 30, 40 or 50 contiguous nucleotides with the corresponding nucleotide sequence from the one or more cells or organisms.

Ligation may be between double stranded or single stranded nucleic acid molecules, depending upon which ligase is utilised.

Thus, in one embodiment, the enzyme utilised in the methods of the invention comprises, consists essentially of or consists of a ligase. Ligases require ATP in order to have catalytic activity. Thus, in the presence of the one or more cells or organisms in the sample, there will be the associated marker for viability, ATP, present in the sample. This ATP activates the ligase, which accordingly catalyses the ligation of the nucleic acid molecule and one or more further nucleic acid molecules. Thus, the novel ligated nucleic acid molecule may then be detected which gives a sensitive and reliable signal to indicate the presence of the one or more cells or organisms in the sample. In the absence of the ATP, which is associated with viability of the one or more cells or organisms, the ligase will not be activated and so the nucleic acid molecule and further nucleic acid molecule(s) will not be ligated to produce the novel detectable nucleic acid molecule.

If the nucleic acid molecule and further nucleic acid molecule are single stranded a suitable ligase such as T4 RNA ligase may be employed. If the nucleic acid molecule and further nucleic acid molecule are double stranded a suitable ligase such as T4 RNA ligase may be employed.

As aforementioned, commercially available ligases tend to be provided in a pre-activated form, meaning they do not require activation by ATP in order to have ligase capability. Of course, an enzyme in this form is not of use in the present invention, since the ligase is utilised in order to detect ATP, which is an indicator of the presence of, or in certain embodiments contamination by, one or more cells or organisms in the sample. Thus, the ligase may need to be appropriately treated in order to remove the activating molecule from the enzyme. Any suitable means of deadenylation may be utilised. This may involve incubation with (sodium) pyrophosphate for example. Suitable conditions are provided in the experimental section below.

In an alternative embodiment, the enzyme, used in the method comprises *E. coli* DNA ligase. This enzyme requires NAD+ for activity as opposed to ATP. Thus, in this case the molecule associated with viability of the cell or organism comprises, consists essentially or consists of NAD+. The de-activation of NAD+dependent ligase is carried out in the same way as for ATP dependent enzyme. NAD+instead of ATP functions as the AMP donor to the enzyme, so the activated product is the same. Thus, any suitable means of deadenylation may be utilised. This may involve incubation with (sodium) pyrophosphate for example. Suitable conditions are provided in the experimental section below.

In a most preferred "detection" embodiment, the one or more cells or organisms which are detected in the sample comprise, consist essentially of or consist of micro-organisms, in particular bacteria and/or yeast, such as *Candida* species for example. The levels of micro-organisms such as these are especially relevant in a public health and hygiene context. Preferably, the one or more organisms comprise, consist essentially of or consist of bacteria. However, the presence of any molecule associated with viability may be indicative of contamination. Thus, detection of the molecule associated with viability may per se be considered an indicator of contamination. The molecule may be derived from any source, be it microbial and/or plant and/or animal.

The bacteria may be any bacterial species which may be considered a contaminant in a sample. The method of the invention has broad applicability as discussed above, and so many different species and strains may be detected in the methods. Of course, multiple types of organisms may be detected at the same time, since markers associated with viability, such as ATP, are omnipresent.

More specific detection of certain cells and organisms may require specific filtration in order to separate the cell or organism to be detected from other ATP producing cells. Such filters and filtration systems and methods are well known in the art and commercially available (for example see www.n-hdiag.com).

Additionally, specific cells and organisms may also be selected and filtered or concentrated by utilising specific reagents which can bind to the cells or organisms. Examples include antibodies and derivatives and fragments thereof which retain specific binding affinity.

In one embodiment, the bacteria comprises or consists essentially of or consists of any one or more of *Staphylococcus* species, in particular *Staphylococcus aureus* and preferably methicillin resistant strains, *Enterococcus* species, *Streptococcus* species, *Mycobacterium* species, in particular *Mycobacterium tuberculosis, Vibrio* species, in particular *Vibrio cholerae, Salmonella, Escherichia coli* etc.

As aforementioned, the methods of the invention may also be applicable to determining growth and/or survival of a cell sample. Thus, the viability of cell cultures may be monitored utilising the methods of the invention. In one embodiment, toxicology testing may be carried out using the methods of the invention.

In a particularly preferred embodiment of the invention, the enzyme is immobilized on a solid support. The immobilization of the enzyme on a solid support allows effective capture of molecules associated with viability which are to be detected and which are derived from the one or more cells or organisms. The interaction of the immobilized enzyme with the molecule associated with viability allows the enzyme to act on the nucleic acid molecule, thus leading to the generation of a novel nucleic acid molecule.

Thus, in one embodiment, the samples which are utilised in the methods of the invention are of larger volume than those of prior art methods. Exemplary sample volumes may be between about 1 and 20 ml, preferably between about 1 and 10 ml even more preferable between about 1 and 5 ml. For example, 1 to 5 ml of sample may be used with an immobilised ligase column and all the ATP released from the cells (for example bacterial cells) in this volume can be accessed. Thus, preferably in this embodiment, the enzyme comprises, consist essentially of or consists of a ligase and the molecule associated with viability comprises, consist essentially of or consists of ATP.

The immobilised enzyme may be washed to remove inhibitory materials that may affect the subsequent detection process. This is possible because the enzyme-viability marker link or bond, preferably an ATP-ligase link, is stable during the washing process. Thus, in one embodiment, the method further comprises, consist essentially of or consists of a washing-step prior to detection of the novel nucleic acid molecule. Washing may utilise any suitable buffer or wash solution, and may include components such as EDTA and Tris-HCl. Suitable wash solutions are well known to those of skill in the art.

Any suitable solid support may be employed. The nature of the solid support is not critical to the performance of the invention provided that the enzyme may be immobilized thereon without adversely affecting enzyme activity, including the ability of the enzyme to interact with the molecule associated with viability of the one or more cells or organisms. Non-limiting examples of solid supports include any of beads, such as polystyrene beads and derivatives thereof and paramagnetic beads, affinity columns, microtitre plates etc.

Similarly, immobilization chemistry is routinely carried out by those skilled in the art. Any means of immobilization may be utilised provided that it does not have an adverse effect on the methods of the invention, especially in terms of specificity and sensitivity of detection of the molecule associated with viability from the one or more cells or organisms.

Preferred Detection Techniques

In a preferred embodiment of the invention, the novel nucleic acid molecule, produced according to the enzyme activity in the presence of a molecule associated with viability of the one or more cells or organisms, is detected using nucleic acid amplification techniques.

This serves to make the methods of the invention maximally sensitive. Such amplification techniques are well known in the art, and include methods such as PCR, NASBA (Compton, 1991), 3SR (Fahy et al., 1991), Rolling circle replication, Transcription Mediated Amplification (TMA), strand displacement amplification (SDA) Clinical Chemistry 45: 777-784, 1999; and the DNA oligomer self-assembly processes described in U.S. Pat. No. 6,261,846 (incorporated herein by reference).

Amplification is achieved with the use of amplification primers specific for the sequence of the novel nucleic acid molecule which is to be detected. In order to provide specificity for the nucleic acid molecules primer binding sites corresponding to a suitable region of the sequence may be selected. The skilled reader will appreciate that the nucleic acid molecules may also include sequences other than primer binding sites which are required for detection of the novel nucleic acid molecule produced by the enzyme in the presence of the molecule associated with viability in the sample, for example RNA Polymerase binding sites or promoter sequences may be required for isothermal amplification technologies, such as NASBA, 3SR and TMA.

Primer binding sites may bridge the nucleic acid molecule and further nucleic acid molecule ligation boundary such that an amplification product is only generated if ligation has occurred, for example.

Suitable primers for use in the methods of the invention are set forth as SEQ ID Nos 12 to 15 and described in more detail in the experimental section below.

TMA (Gen-probe Inc.) is an RNA transcription amplification system using two enzymes to drive the reaction, namely RNA polymerase and reverse transcriptase. The TMA reaction is isothermal and may amplify either DNA or RNA to produce RNA amplified end products. TMA may be combined with Gen-probe's Hybridization Protection Assay (HPA) detection technique to allow detection of products in a single tube. Such single tube detection is a preferred method for carrying out the invention. The list above is not intended to be exhaustive. Any nucleic acid amplification technique may be used provided the appropriate nucleic acid product is specifically amplified.

Thus, in a preferred aspect of the invention the method of the invention is carried out using nucleic acid amplification techniques in order to detect the novel nucleic acid molecule produced as a direct result of the addition or removal of a chemical moiety by the activated enzyme which indicates the presence of a molecule associated with viability of a cell or organism in the sample. In a preferred embodiment the technique used is selected from PCR, NASBA, 3SR, TMA, SDA and DNA oligomer self-assembly. Detection of the amplification products may be by routine methods, such as, for example, gel electrophoresis but is preferably carried out using real-time detection methods.

A number of techniques for real-time detection of the products of an amplification reaction are known in the art. These include use of intercalating fluorescent dyes such as SYBR Green I (Sambrook and Russell, Molecular Cloning—A Laboratory Manual, Third edition), which allows the yield of amplified DNA to be estimated based upon the amount of fluorescence produced. Many of the real-time detection methods produce a fluorescent read-out that may be continuously monitored; specific examples including molecular beacons and fluorescent resonance energy transfer probes. Real-time techniques are advantageous because they keep the reaction in a “single tube”. This means there is no need for downstream analysis in order to obtain results, leading to more rapidly obtained results. Furthermore keeping the reaction in a “single tube” environment reduces the risk of cross contamination and allows a quantitative output from the methods of the invention. This may be particularly important in the context of the present invention where health and safety concerns may be of paramount importance (such as in water supplies for human consumption etc.).

Real-time quantitation of PCR reactions may be accomplished using the TaqMan® system (Applied Biosystems), see Holland et al; Detection of specific polymerase chain reaction product by utilising the 5'-3' exonuclease activity of *Thermus aquaticus* DNA polymerase; Proc. Natl. Acad. Sci. USA 88, 7276-7280 (1991), Gelmini et al. Quantitative polymerase chain reaction-based homogeneous assay with fluorogenic probes to measure C-Erb-2 oncogene amplification. Clin. Chem. 43, 752-758 (1997) and Livak et al. Towards fully automated genome wide polymorphism screening. Nat. Genet. 9, 341-342 (19995) (incorporated herein by reference). Taqman® probes are widely commercially available, and the Taqman® system (Applied Biosystems) is well known in the art. Taqman® probes anneal between the upstream and downstream primer in a PCR reaction. They contain a 5-fluorophore and a 3'-quencher. During amplification the 5'-3' exonuclease activity of the Taq polymerase cleaves the fluorophore off the probe. Since the fluorophore is no longer in close proximity to the quencher, the fluorophore will be allowed to fluoresce. The resulting fluorescence may be measured, and is in direct proportion to the amount of target sequence that is being amplified.

In the Molecular Beacon system, see Tyagi & Kramer. Molecular beacons—probes that fluoresce upon hybridization. Nat. Biotechnol. 14, 303-308 (1996) and Tyagi et al. Multicolor molecular beacons for allele discrimination. Nat. Biotechnol. 16, 49-53 (1998) (incorporated herein by reference), the beacons are hairpin-shaped probes with an internally quenched fluorophore whose fluorescence is restored when bound to its target. The loop portion acts as the probe while the stem is formed by complimentary “arm” sequences at the ends of the beacon. A fluorophore and quenching moiety are attached at opposite ends, the stem keeping each of the moieties in close proximity, causing the fluorophore to be quenched by energy transfer. When the beacon detects its target, it undergoes a conformational change forcing the stem apart, thus separating the fluorophore and quencher. This causes the energy transfer to be disrupted to restore fluorescence.

Any suitable fluorophore is included within the scope of the invention. Fluorophores that may possibly be used in the methods of the invention include, by way of example, FAM, HEX™, NED™, ROX™, Texas Red™ etc. Quenchers, for example Dabcyl and TAMRA, represent well known quencher molecules that may be used in the method of the invention. However, the invention is not limited to these specific examples.

A further real-time fluorescence based system which may be incorporated in the methods of the invention is Zeneca's Scorpion system, see Detection of PCR products using self-probing amplicons and fluorescence by Whitcombe et al. Nature Biotechnology 17, 804-807 (1 Aug. 1999). This reference is incorporated into the application in its entirety. The method is based on a primer with a tail attached to its 5' end by a linker that prevents copying of the 5' extension. The probe element is designed so that it hybridizes to its target only when the target site has been incorporated into the same molecule by extension of the tailed primer. This method produces a rapid and reliable signal, because probe-target binding is kinetically favoured over intra-strand secondary structures.

Additional real-time detection techniques which are well known to those skilled in the art and which are commercially available include Lightcycler® technology and Amplifluour® primer technology.

Thus, in a further aspect of the invention the products of nucleic acid amplification are detected using real-time techniques. In one specific embodiment of the invention the real-time technique consists of using any one of the Taqman® system, Lightcycler® system, Amplifluour® system, the Molecular Beacons® system or the Scorpion® probe system.

In a most preferred embodiment, the reaction mixture will contain all of; the sample under test, the nucleic acid molecule and further nucleic acid molecule, the required enzyme, in particular a ligase and all reagents, buffers and enzymes required for amplification of the novel (preferably ligated) nucleic acid molecule in addition to the reagents required to allow real time detection of amplification products. Thus the entire detection method for the molecule associated with viability (from the one or more cells or organisms of interest) will occur in a single reaction, with a quantitative output, and without the need for any intermediate washing steps. Use of a "single tube" reaction is advantageous because there is no need for downstream analysis in order to obtain results, leading to more rapidly obtained results. Furthermore keeping the reaction in a "single tube" environment reduces the risk of cross contamination and allows a quantitative output from the methods of the invention. Also, single tube reactions are more amenable to automation, for example in a high throughput context.

Alternatively, the method of the invention may be carried out in step-wise fashion. Thus, in a first step it may first be necessary to prepare the enzyme in a form suitable for use in the method of the invention. For example, a commercially provided ligase may need to be stripped of AMP so it is no longer active and requires ATP, as provided by any cells or organisms, which may be contaminant organisms in one embodiment, in the sample, in order to be active. This may be carried out using suitable deadenylation conditions and is discussed above in further detail.

Furthermore, the enzyme may be immobilized initially prior to carrying out the method. Suitable solid supports and methods of immobilization are well known in the art and are described above in more detail.

The enzyme may be added first to the sample under test, allowing any molecule associated with viability of the one or more cells or organisms present in the sample to interact with the enzyme. The enzyme may then add a chemical moiety to or remove a chemical moiety from the nucleic acid molecule. Thus, in one embodiment, the invention may be utilised to concentrate a molecule associated with viability such as ATP. The concentrated ATP bound to the enzyme may then be readily detected in a subsequent step, preferably by amplification of the novel nucleic acid molecule.

The enzyme, which is preferably a ligase may, in a further embodiment, be inactivated before adding reagents necessary for detection, which will most preferably be by amplification. Depending on whether an isothermal amplification technique is used this may influence whether the enzyme, which is preferably a ligase, needs to be inactivated before carrying out the detection step. If real time detection is being utilised the required reagents may be added together with the reagents required for the amplification stage.

Primers specific for the novel detectable nucleic acid molecule to be amplified are utilised in the methods and kits of the invention. Any primer that may direct sequence specific amplification of the novel detectable nucleic acid molecule with minimum background, non-specific amplification, may be utilised. Primers may comprise DNA or RNA and synthetic equivalents depending upon the amplification technique being utilised. For example, for standard PCR a short single stranded DNA primer pair tends to be used, with both primers bordering a region of interest to be amplified. The types of primers that may be used in nucleic acid amplification technology such as PCR, 3SR, NASBA and TMA are well known in the art.

Suitable probes for use in the real-time methods may also be designed, in order that they may be used in conjunction with the nucleic acid molecules in the methods of the invention. Thus, for example, when using the Taqman® technique, the probes may be of sequence such that they can bind between primer binding sites on the novel nucleic acid molecule which is produced as a result of the enzyme activity caused in turn by the molecule associated with viability of a contaminating cell or organism in the sample. Similarly molecular beacon probes may be designed that bind to a relevant portion of the nucleic acid sequence incorporated into the methods and kits of the invention. If using the Scorpion probe technique for real time detection the probe will need to be designed such that it hybridizes to its target only when the target site has been incorporated into the same molecule by extension of the tailed primer. Amplifluour technology will require suitable design of the primers, but does not require a separate probe. Therefore, the invention further provides for the inclusion of probes or suitably designed primers, suitable for use in real-time detection methods in the present invention.

Alternative techniques may be used to detect the addition of a chemical moiety to, or removal of a chemical moiety from, the nucleic acid molecule, which leads to the generation of a novel detectable nucleic acid molecule. Examples of alternative detection techniques include mass spectrometry, including matrix assisted laser desorption (MALDI) mass spectrometry and MALDI-Time of Flight (MALDI-TOF) mass spectrometry, chromatography and use of microarray technology (Illumina, Affymetrix, Nanogen). Mass spectrometry allows the expected molecular weight of the novel nucleic acid molecules to be accurately measured. MALDI-TOF relies upon a high voltage potential which rapidly extracts ions and accelerates them down a flight tube. A detector at the end of the flight tube is used to determine the time elapsed from the initial laser pulse to detection of the ions. The flight time is proportional to the mass of the ion. Thus, in the method of the invention the difference in the mass of the nucleic acid molecules compared to the novel detectable nucleic acid molecule is sufficient to allow specific and sensitive detection.

Similarly, by using a microarray with suitable probes attached to the solid support, the novel nucleic acid molecules produced in the methods of the invention may be identified in a downstream process.

These alternative techniques may preferably be used in conjunction with nucleic acid amplification techniques in order to characterise the amplification products. This will help to remove false positive results, where an amplified product had been produced which is not the expected product. Thus, the advantages of an amplification step to increase sensitivity is combined with a step to accurately characterise the amplification products thus making the methods of the invention even more accurate.

In one embodiment, the invention provides for a method in which the sample is initially filtered in order to concentrate the one or more cells or organisms (as described above). More specific detection of certain cells or organisms may require specific filtration in order to separate the cell or organism to be detected from other ATP producing cells. Such filters and filtration systems and methods are well known in the art and commercially available (for example see www.nhdiag.com).

Additionally, specific cells or organisms may also be selected by utilising specific reagents which can bind to the cells or organisms. Examples include antibodies and derivatives thereof which retain specific binding affinity.

In a further embodiment, the method further comprises, consists essentially of or consists of lysing other cells in the sample which are not target cells or organisms but which would otherwise contribute markers associated with viability to the assay system. This lysis of other cells is a means by which these non-target cells or organisms can be prevented from influencing the detection of the desired cells or organisms.

In a preferred embodiment, the method further comprises, consists essentially of or consists of removing or exhausting from the sample any molecules associated with viability of the one or more cells or organisms which are not provided by the one or more cells or organisms. Thus, once the non-target organisms or cells have been lysed their molecules associated with viability may be released into the sample. It is of benefit to remove these molecules since they may lead to false positive results if not otherwise removed. The non-contaminant cells may be harmless cells or cells which are intended to be present in the sample, such as platelets in a platelet sample etc.

In one embodiment, the molecule associated with viability of the one or more cells or organisms comprises ATP. Preferably, the molecule associated with viability of the one or more cells or organisms, which is preferably ATP, is removed by utilising it, or exhausting the supplies thereof, in a reaction catalysed by an enzyme.

The enzyme which may exhaust the molecule associated with viability provided by non-target cells or organisms, comprises, consists essentially of or consists of, in one embodiment any one or more of luciferase, phosphatase and pyrophosphatase. These enzymes may be added to the sample to break down ATP, which is the preferred molecule associated with viability in the present invention. In the case of luciferase it is easy for the user to assess when the unwanted ATP has been used up because the luminescence ceases to be produced.

Preferably, once the molecule associated with viability, as provided by the non-target cells or organisms, has been exhausted from the sample the method further comprises, consists essentially of or consists of lysing the cells of the one or more cells or organisms in order to release the molecule associated with viability of the one or more cells or organisms. This lysis may require different conditions to those which may have been utilised to lyse the non-target (or non-contaminant in one embodiment) cells, since this provides a level of specificity of lysis such that cells of interest are not initially lysed with other non-target cells.

The procedures described above are also applicable to the removal of contaminating ATP from other sources such as animal or plant tissue. This is relevant in food applications, for example where it is necessary to remove the ATP background prior to lysing the target cells or organisms. This then gives a measure of the (bacterial) contamination of the food sample. Removal of the ATP background may be by luciferase, or phosphatase or pyrophosphatase for example. The procedure for determining bacterial contamination of platelets, for example, may involve lysing the platelets first using detergent, followed by destruction of the released ATP using an efficient process such as alkaline phosphatase in large excess, followed by the application of harsh conditions to lyse the target contaminating organisms leading to release of the much smaller quantity of ATP for detection.

Suitable cell lysis conditions are well known in the art and include by way of example and not limitation, treatment with heat, phenol, chloroform, proteinase K, alcohols etc. and combinations thereof, and/or freeze/thaw treatments or mechanical disruption for example (such as high speed centrifugation).

The method of the invention may further/additionally comprise, consist essentially of or consist of treatment of the sample with one or more nucleases in order to degrade nucleic acid molecules associated with the one or more cells or organisms. This is an approach utilised to ensure that the nucleic acid molecules found in the one or more cells or organisms to be detected can not interfere with the detection of the novel nucleic acid molecule produced according to the methods of the invention. Any nuclease capable of digesting nucleic acid molecules found in the one or more cells or organisms, from which the molecule associated with viability is to be detected may be employed and may comprise, consist essentially of or consist of an endonuclease and/or an exonuclease for example. Many such nucleases are commercially available and would be well known to the skilled person.

The nucleic acid molecules and optionally further nucleic acid molecules which generate the novel nucleic acid molecule according to the methods of the invention may be designed such that they are protected from nuclease activity. For example, the ends of the nucleic acid molecules may be blocked so that once the novel nucleic acid molecule has been generated, it is not susceptible to nuclease action and can thus be detected to indicate the presence of a molecule associated with viability, for example from a contaminant organism.

In a further preferred embodiment of the invention, the nucleic acid molecule is immobilized on a solid support. Direct immobilization may be achieved via a covalent linkage for example.

Techniques are known in the art for direct covalent linkage of both nucleic acid and protein components to a solid support. For example, amine-derivatized nucleic acid molecules may be coupled to a solid support using any one of a number of chemical cross-linking compounds.

It is also within the scope of the invention for the nucleic acid molecules and/or the enzyme to be attached indirectly to the solid support. For example, "indirect" attachment may be achieved through linker molecules. Suitable linker molecules include components of biological binding pairs which bind with high affinity, for example biotin/streptavidin or biotin/avidin.

For most applications of the method of the invention, the nucleic acid molecules and/or enzyme will be attached to the (respective) solid support at the start of the reaction. Most preferably, the nucleic acid molecules and/or enzyme will be supplied pre-immobilized on a solid support, or else immobilization will occur in a separate immobilization step. However, other possibilities are not excluded.

In one specific embodiment, the nucleic acid molecule is immobilized on the same support as the enzyme. This acts to effectively bring the nucleic acid molecule into proximity to the enzyme. Thus, if the enzyme is activated through interaction with a molecule associated with viability to be detected from the one or more cells or organisms it will immediately be able to act on the nucleic acid molecule to generate a novel nucleic acid molecule, which may then be detected to indicate the presence of the molecule associated with viability, which may indicate for example that one or more contaminating cells or organisms are present in the sample.

In a further embodiment, the further nucleic acid molecule is also immobilized on a solid support. This may serve to enhance the sensitivity of the method still further because the further nucleic acid molecule is in proximity to both the enzyme and the nucleic acid molecule. Thus, if the ligase is activated through interaction with a molecule associated with viability which acts as an indicator of the one or more cells or organisms to be detected it will immediately be able to act on the nucleic acid molecule and further nucleic acid molecule to generate a novel nucleic acid molecule, which may then be detected for example to indicate the presence of one or more contaminating organisms in the sample or to indicate that a cell culture remains viable. Preferably, in this embodiment, the molecule associated with viability comprises, consists essentially of or consists of ATP. Preferred set-ups are described below with reference to FIGS. 2 and 3.

In one embodiment, the enzyme and/or nucleic acid molecule and/or further nucleic acid molecule may all be immobilized on the same solid support in order to ensure maximal proximity of the interacting components. This helps to achieve high levels of sensitivity of detection of the molecule associated with viability of the one or more cells or organisms in the sample. As mentioned above, any suitable solid support may be employed and any suitable means for immobilizing each of the components may likewise be utilised.

Screening Methods

The methods of the present invention also have utility in the important field of microbial resistance to existing treatments. Many bacteria are now resistant to a large number of currently available antimicrobial treatments, and certain strains, such as Methicillin Resistant *Staphylococcus aureus* (MRSA) pose dangerous health risks particularly in a clinical context.

There is, therefore, a requirement for techniques and assay kits which allow resistance to anti-microbial agents to be readily determined.

Therefore, according to a second aspect, the invention provides a method of screening for resistance of a cell or organism to an agent directed against said cell or organism, the method comprising, consisting essentially of or consisting of the steps of, in a sample:

(a) exposing the cell or organism to the agent;

(b) contacting the sample with an enzyme, which enzyme is capable of adding or removing a chemical moiety to or from a nucleic acid molecule in the presence of a molecule associated with viability of the cell or organism, thereby generating a novel detectable nucleic acid molecule; and (c) detecting whether there is resistance by detecting the novel nucleic acid molecule generated only in the presence of the molecule associated with viability of the cell or organism;

wherein if there is resistance, the novel nucleic acid molecule will be detected.

The same method may also be used as a compound screening method to determine if a new compound, agent or molecule has effect against a particular one or more target cells or organisms.

Thus, in a third aspect the invention provides a method of screening for agents which are capable of killing or preventing growth of one or more cells or organisms, the method comprising, consisting essentially of or consisting of the steps of, in a sample:

(a) exposing the one or more cells or organisms to the agent;

(b) contacting the sample with an enzyme, which enzyme is capable of adding or removing a chemical moiety to or from a nucleic acid molecule in the presence of a molecule associated with viability of the one or more cells or organisms, thereby generating a novel detectable nucleic acid molecule; and (c) detecting whether the agent has the ability to kill or prevent growth of the one or more cells or organisms by detecting the novel nucleic acid molecule generated only in the presence of the molecule associated with viability of the cell or organism; wherein if the agent is capable of killing or preventing growth of the cell or organism, the novel nucleic acid molecule will not be detected.

This aspect of the invention may also be utilised as a rapid viability test in compound screening. Thus, a compound, agent or molecule may be screened according to the method to determine whether it is toxic to cells such as mammalian cells. Thus, a positive result in the method in terms of detecting the novel nucleic acid molecule would indicate that the compound is of low toxicity to the mammalian or plant cells. In this case, a suitable sample would comprise the relevant mammalian cells. The screening may be carried out as a prelude to determining whether the compound, agent or molecule is effective to kill, prevent growth or proliferation of a disease causing organism or otherwise prevent disease progression caused by the organism.

Thus, in a further aspect the invention provides a method of determining the toxicity of a candidate pharmaceutical agent or agricultural agent to mammalian or plant cells comprising, consisting essentially of or consisting of the steps of, in a sample of mammalian or plant cells:

(a) exposing the cells to the (pharmaceutical or agricultural) agent;

(b) contacting the sample with an enzyme, which enzyme is capable of adding or removing a chemical moiety to or from a nucleic acid molecule in the presence of a molecule associated with viability of the cells, thereby generating a novel detectable nucleic acid molecule; and (c) detecting whether the (pharmaceutical or agricultural) agent is toxic to the cells by detecting the novel nucleic acid molecule generated only in the presence of the molecule associated with viability of the cells;

wherein if the molecule is toxic to the cells, the novel nucleic acid molecule will not be detected.

For the avoidance of doubt, this method is generally intended to be an in vitro method carried out on an isolated sample of mammalian cells. In the case of plant products, the testing may be carried out with any suitable plant sample which provides the necessary cells to determine toxicity.

Thus, the plant cells may be derived from the roots, leaves or stems of the plant for example.

The pharmaceutical agent may be any candidate pharmaceutical for treatment of any specified disease. Prior to use in the clinic extensive toxicology testing is required for a new drug. The methods of the present invention may prove useful to assist this process.

Similarly, products for use with plants such as pesticides and herbicides (weedkillers) are of little value if they are toxic to the plants which are to be protected from the pests or weeds. Thus, the method according to the invention may be utilised in order to ensure that the candidate agent is non-toxic to the plants which are intended to benefit from use of the agent.

The method of the invention may also prove to have diagnostic utility, whereby an infection may be specifically and sensitively detected in the early stages when only minimal levels of the infecting cell or organism are present.

Therefore, in a further aspect there is provided a method of diagnosing an infection, or a disease associated with the presence of a cell or organism in a subject, comprising, consisting essentially of or consisting of the steps of, in a sample obtained from the subject:

a) contacting the sample with an enzyme, which enzyme is capable of adding or removing a chemical moiety to or from a nucleic acid molecule in the presence of a molecule associated with viability of the cell or organism, thereby generating a novel detectable nucleic acid molecule; and b) detecting the presence of the viable cell or organism by detecting the novel nucleic acid molecule generated only in the presence of the molecule associated with viability of the cell or organism, wherein if the novel nucleic acid molecule is detected the subject is considered to be infected, or to have the disease.

In this context the "sample" will generally be a clinical sample. The sample being used will depend on the condition that is being tested for. Typical samples which may be used, but which are not intended to limit the invention, include whole blood, serum, plasma, platelet and urine samples etc. taken from a patient, most preferably a human patient.

In a most preferred embodiment, the test will be an in vitro test carried out on a sample removed from a subject.

In a further embodiment, the above-described diagnostic methods may additionally include the step of obtaining the sample from a subject. Methods of obtaining a suitable sample from a subject are well known in the art. Alternatively, the method may be carried out beginning with a sample that has already been isolated from the patient in a separate procedure. The diagnostic methods will most preferably be carried out on a sample from a human, but the method of the invention may have diagnostic utility for many animals.

The diagnostic methods of the invention may be used to complement any already available diagnostic techniques, potentially as a method of confirming an initial diagnosis. Alternatively, the methods may be used as a preliminary diagnosis method in their own right, since the methods provide a quick and convenient means of diagnosis. Furthermore, due to their inherent sensitivity, the diagnostic methods of the invention require only a minimal sample, thus preventing unnecessary invasive surgery. Also, a large but non-concentrated sample may also be tested effectively according to the methods of the invention.

Thus, the methods of the invention have multiple applications beyond detection of contaminating organisms in a sample. The description provided above with respect to the first aspect of the invention applies mutatis mutandis to the further aspects of the invention and is not repeated for reasons of conciseness.

In preferred embodiments the molecule associated with viability is derived from a bacterium.

The bacterium may be any bacterium which is capable of causing infection or disease in a subject, preferably a human subject. In one embodiment, the bacteria comprises or consists essentially of or consists of any one or more of *Staphylococcus* species, in particular *Staphylococcus aureus* and preferably methicillin resistant strains, *Enterococcus* species, *Streptococcus* species, *Mycobacterium* species, in particular *Mycobacterium tuberculosis, Vibrio* species, in particular *Vibrio cholerae, Salmonella* and/or *Escherichia coli* etc.

In one embodiment, according to the second, third and fourth aspects of the invention, the molecule which is being tested in the method (either for resistance or ability to treat an infection or toxicity to cells) is an antimicrobial compound. In the compound screening method, any molecule may be tested. Examples include antimicrobial agents, nucleic acid molecules including siRNA molecules and antisense molecules, small molecules, antibodies and all derivatives thereof including Fab fragments, variable region fragments and single domain antibodies for example provided they retain binding affinity etc. The method may be carried out in a high throughput context to screen large numbers of molecules in a short period of time.

The antimicrobial agent, in one embodiment, may be taken from the two main types of antimicrobial agents, antibiotics (natural substances produced by microorganisms) and chemotherapeutic agents (chemically synthesized), or may be a hybrid of the two such as semi-synthetic antibiotics (a subsequently modified naturally produced antibiotic) or synthetic antibiotics (synthesised versions of natural antibiotics).

Suitable candidate antimicrobial agents may, following a positive result in the methods of the invention in terms of ability to kill or prevent growth of a cell or organism and/or lack of toxicity to mammalian cells be tested for at least one or more of the following properties:

(1) the agent should be non-toxic to the subject and without adverse side effects, (2) the agent should be non-allergenic to the subject, (3) the agent should not eliminate the natural flora of the subject, (4) the agent should be stable, (5) the agent should preferably be cheap and readily available/easy to manufacture; and (6) the agent should be sufficiently potent that pathogen resistance does not develop (to any appreciable degree). This feature may be tested according to the method described according to a second aspect of the invention (above).

In one embodiment, a combination of multiple suitable antimicrobial agents may be tested for ability to treat an infection and/or for resistance thereto.

Antibiotics or derivatives thereof which may be tested for resistance and perhaps also for their novel ability to treat certain infections may be selected from the following groups, provided by way of example and not limitation; beta-lactams such as penicillin, in particular penicillin G or V, and cephalosporins such as cephalothin, semi-synthetic penicillins such as ampicillin, methicillin and amoxicillin, clavulanic acid preferably used in conjunction with a semi-synthetic penicillin preparation (such as clavamox or augmentin for example), monobactams such as aztreonam, carboxypenems such as imipenem, aminoglycosides such as streptomycin, kanamycin, tobramycin and gentamicin, glycopeptides such as vancomycin, lincomycin and clindamycin, macrolides such as erythromycin and oleandomycin, polypeptides such as polymyxin and bacitracin, polyenes such as amphotericin and nystatin, rifamycins such as rifampicin, tetracyclines such as tetracycline, semi-synthetic tetracyclines such as doxycycline, chlor tetracycline, chloramphenicol, quinolones such as nalidixic acid and fluoroquinolone and competitive inhibitors such as sulfonamides, for example gantrisin and trimethoprim. Ceftriaxone and/or nitroflurazone may also be utilised.

Kits of the Invention.

The invention also provides kits which enable and are suitable for the carrying out of the methods of the invention.

Therefore, in a further aspect, the invention provides a kit for detecting a molecule associated with viability of one or more (viable) cells or organisms in a sample comprising, consisting essentially of or consisting of:

(a) a nucleic acid molecule; and
(b) an enzyme capable of adding or removing a chemical moiety to or from the nucleic acid molecule in the presence of the molecule associated with viability of the one or more cells or organisms, thereby generating a novel detectable nucleic acid molecule.

In a still further aspect, the invention also provides a kit for screening for resistance of a cell or organism to a molecule directed-against said cell or organism, the kit comprising, consisting essentially of or consisting of:

(a) a nucleic acid molecule; and
(b) an enzyme capable of adding or removing a chemical moiety to or from the nucleic acid molecule in the presence of a molecule associated with viability of the cell or organism, thereby generating a novel detectable nucleic acid molecule.

In an even further aspect, the invention provides a kit for screening for molecules which are capable of killing or preventing growth of a cell or organism, the kit comprising, consisting essentially of or consisting of:

(a) a nucleic acid molecule; and
(b) an enzyme capable of adding or removing a chemical moiety to or from the nucleic acid molecule in the presence of a molecule associated with viability of the cell or organism, thereby generating a novel detectable nucleic acid molecule.

Furthermore, the invention also provides a kit for diagnosing an infection, or a disease associated with the presence of a cell or organism in a subject, comprising, consisting essentially of or consisting of:

(a) a nucleic acid molecule; and
(b) an enzyme capable of adding or removing a chemical moiety to or from the nucleic acid molecule in the presence of a molecule associated with viability of the cell or organism, thereby generating a novel detectable nucleic acid molecule.

In a further aspect the invention provides a kit for determining the toxicity of a candidate pharmaceutical agent or agricultural agent to mammalian or plant cells comprising, consisting essentially of or consisting of:

(a) a nucleic acid molecule; and
(b) an enzyme capable of adding or removing a chemical moiety to or from the nucleic acid molecule in the presence of a molecule associated with viability of the cell or organism, thereby generating a novel detectable nucleic acid molecule.

As mentioned above, the pharmaceutical agent may be any candidate pharmaceutical for treatment of any specified disease. Similarly, products for use with plants such as pesticides and weedkillers are of little value if they are toxic to the plants which are to be protected from the pests or weeds. Thus, the kit according to the invention may be utilised in order to ensure that the candidate agent is non-toxic to the plants which are intended to benefit from use of the agent.

Preferably, these kits also comprise, consist essentially of or consist of (c) a further nucleic acid molecule.

All aspects of the method of the invention may be applied to the kits of the invention and accordingly the description above applies equally here.

In one embodiment, the novel nucleic acid molecule is formed by ligation. Preferably, the novel nucleic acid molecule is generated by ligation of the nucleic acid molecule with the further nucleic acid molecule. The description, provided with respect to the methods of the invention, of suitable nucleic acid molecules and further nucleic acid molecules applies mutatis mutandis to the kit aspects of the invention.

As aforementioned, the preferred means for producing the novel nucleic acid molecule involves ligation. Therefore, preferably, the enzyme capable of adding or removing a chemical moiety to or from the nucleic acid molecule in the presence of a molecule associated with viability of the one or more cells or organisms, thereby generating a novel detectable nucleic acid molecule comprises, consists essentially of or consists of a ligase.

Any suitable ligase may be employed, which depends upon a molecule associated with viability (as defined above, such as ATP for example) for its activity. Thus, ligase activity directly correlates with the presence of the molecule associated with viability of the (viable) cell or organism in the sample, because if the marker is present the ligase will be activated and thus will catalyse generation of the novel nucleic acid molecule which may be detected. Suitable non-limiting examples of ligases include the commercially available T4 DNA ligase or T4 RNA ligase. Preferably, as described above, the ligase is provided in a de-activated form, and so the activator co-factor, which may be ATP or $NAD^+$ for example, is not present. This means that the ligase must be activated by the marker associated with viability from the cells or organisms to be detected. Alternatively, the kit may supply the ligase in activated form but may also provide means for de-activating the ligase prior to use. Details of how to remove an AMP molecule or $NAD^+$ from a ligase are provided above and apply equally to the kit aspects of the invention, such as incubation with pyrophosphate for example. Details of deadenylation are provided in the experimental section below.

The most preferred molecule associated with viability of the organism comprises, consists essentially of or consists of ATP. However, alternative molecules may be monitored, such as $NAD^+$. In this case, *E. Coli* DNA ligase may be employed since this ligase requires $NAD^+$ for its activity, rather than ATP.

As described in more detail above with respect to the methods of the invention, the ATP may be derived from any suitable source.

In a most preferred embodiment, the one or more cells or organisms which are detected in the sample comprise, consist essentially of or consist of micro-organisms, in particular bacteria and/or yeast. The levels of micro-organisms such as these are especially relevant in a public health and hygiene context. Preferably, the one or more organisms comprise, consist essentially of or consist of bacteria. However, the kits of the invention are useful for detecting molecules associated with viability from all sources, including from plant and animal cells. This may be useful in applications such as monitoring cell cultures and also determining whether there is any source of contamination present in a particular sample.

The bacteria may be any bacterial species which may be considered a contaminant in a sample. The method of the invention has broad applicability as discussed above, and so many different species and strains may be detected in the methods. Of course, multiple types of cells and organisms may be detected at the same time, since markers associated with viability, such as ATP, are omnipresent.

More specific detection of certain cells or organisms may require specific filtration in order to separate the cell or organism to be detected from other ATP producing cells. Such filters and filtration systems and methods are well known in the art and commercially available (for example see www.n-hdiag.com). The kits of the invention may also incorporate a suitable filter or filtration mechanism or system in order to be able to isolate target cells or organisms prior to determining whether the molecule associated with viability is present.

Additionally, specific cells or organisms may also be selected by utilising specific reagents which can bind to the cells or organisms. Thus, the kits of the invention may additionally comprise, consist essentially of or consist of antibodies and all derivatives thereof (such as Fab fragments, single domain antibodies and variable region fragments) which retain specific binding affinity.

In one embodiment, the bacteria comprises or consists essentially of or consists of any one or more of *Staphylococcus* species, in particular *Staphylococcus aureus* and preferably methicillin resistant strains, *Enterococcus* species, *Streptococcus* species, *Mycobacterium* species, in particular *Mycobacterium tuberculosis, Vibrio* species, in particular *Vibrio cholerae, Salmonella, Escherichia coli* etc.

In a particularly preferred embodiment of the invention, the enzyme is immobilized on a solid support. The immobilization of the enzyme on a solid support allows effective capture of the molecules associated with viability from the one or more cells or organisms which are detected. The interaction of the immobilized enzyme with the molecule associated with viability allows the enzyme to act on the nucleic acid molecule, thus leading to the generation of a novel nucleic acid molecule. Thus, the kits of the invention may further comprise a solid support. The enzyme may or may not be provided pre-loaded on the solid-support. If it is not pre-immobilized on the solid support, suitable reagents to allow immobilization may be provided in the kit, optionally together with suitable instructions. Reagents to allow immobilization would be well known to one of skill in the art. Any means of immobilization may be utilised provided that it does not have an adverse effect on the implementation of the methods of the invention, especially in terms of specificity and sensitivity of detection of the molecule associated with viability from the one or more target cells or organisms.

Any suitable solid support may be included in the kits of the invention. The nature of the solid support is not critical to the performance of the invention provided that the enzyme may be immobilized thereon without adversely affecting enzyme activity, including the ability of the enzyme to interact with the molecule associated with viability of the one or more cells or organisms. Non-limiting examples of solid supports include any of beads, such as polystyrene beads and paramagnetic beads and derivatives thereof, affinity columns, microtitre plates etc.

In further embodiments, the nucleic acid molecule and/or further nucleic acid molecule may also be provided immobilized on a solid support in the kits of the invention. The description above applies mutatis mutandis. In a specific embodiment, the nucleic acid molecule and further nucleic acid molecule may be immobilized on the same support as one another. This allows the molecules to be in proximity to ensure that ligation is efficient once the ligase has been activated by the molecule associated with viability.

In a further embodiment, the nucleic acid molecule and/or further nucleic acid molecule may be immobilized on the same support as the enzyme. Thus, if the enzyme is activated (by the molecule associated with viability, which is preferably ATP) it will readily be able to act on the nucleic acid molecule and/or further nucleic acid molecule. This ensures maximal sensitivity of detection.

In a still further embodiment, the kits of the invention further comprise, consist essentially of or consist of reagents necessary for nucleic acid amplification. Preferably, the reagents are for carrying out any one of PCR, Rolling Circle Amplification, NASBA, 3SR and TMA. Reagents for carrying out nucleic acid amplification are commercially available and extremely well characterised in the art. Examples of suitable reagents include suitable primers designed to amplify the novel nucleic acid molecule, polymerases, such as Taq polymerase of which several variants (including hot start variants) are available and buffers such as KCl and $(NH_4)_2SO_4$.

In a preferred embodiment, the kit further comprises, consists essentially of or consists of reagents for detecting the products of nucleic acid amplification in real time. Preferably, the kit includes reagents for carrying out real-time amplification and detection utilising any one of the Taqman® system, Molecular Beacons® system, Lightcycler®, Amplifluour® and Scorpion® probe system. Suitable reagents for use in these methods are well known in the art and are commercially available.

Examples of suitable reagents include sequence specific probes. These probes may bind in between the primers used to amplify the novel nucleic acid molecule, and thus may bind to amplified nucleic acid molecules to provide a direct indicator of the levels of product being formed during amplification. The design of such probes is routine for one of skill in the art. Alternatively, appropriate primers may need to be designed, for example in the Amplifluour and Scorpion systems which allow real time detection of amplification products.

Any suitable fluorophore is included within the scope of the invention. Fluorophores that may possibly be included in the kits of the invention include, by way of example, FAM, HEX™, NED™, ROX™, Texas Red™ etc. Similarly the kits of the invention are not limited to a single quencher. Quenchers, for example Dabcyl and TAMRA are well known quencher molecules that may be used in the method of the invention and included in the kits of the invention.

Kits of the invention may also include further components necessary for the generation and detection of PCR products other than those described above, such as microarrays, which may be used for detection of amplification products, or may be used to amplify (amplification on a chip) and detect the amplification product. Other components may further include "micro fluid cards" as described by Applied Biosystems, Reversed hybridization strips such as those described by LIPA technology (Innogenetics, Zwijnaarde, Belgium, or those described by Ulysis and ULS technology (Kreatech Biotechnologies, Amsterdam, The Netherlands)). Such components are known in the art and are listed by way of example and not limitation for inclusion in the kits of the invention.

The sample for testing with the kits of the invention may be any suitable sample, as defined above. The sample may be a clinical sample, or an in vitro assay system for example.

Samples may be beverage or food samples or preparations thereof, or pharmaceutical or cosmetic products such as personal care products including shampoos, conditioners, moisturisers etc., all of which are tested for microbial contamination as a matter of routine. The sample may comprise tissue or cells and may be a sputum or a blood sample or a platelet sample for example.

As mentioned above, for detection of molecules associated with viability from specific cells or organisms it may be of benefit to incorporate specific filters or filtration systems in the kits of the invention.

Additionally lysis reagents, which lyse other cells which are not target cells or organisms but which would otherwise contribute markers associated with viability to the assay system may be included in the kits of the invention. Suitable reagents, which preferably do not lyse the cells of the cells or organisms which are to be detected include, by way of example and not limitation alcohols, salts etc and possibly also reagents such as proteinase K and chloroform depending upon which cells or organisms are being detected.

The kits of the invention may further comprise, consist essentially of or consist of an enzyme for removing or exhausting from the sample any molecules associated with viability of the one or more cells or organisms which are not provided by the one or more cells or organisms. Preferably, the molecule associated with viability of the one or more cells or organisms comprises ATP. In a specific embodiment, the enzyme comprises any one or more of luciferase, phosphatase and pyrophosphatase, since all of these enzymes may be used to exhaust the ATP signal derived from non-target cells or organisms in the sample which may otherwise give rise to false positive results.

The kits of the invention may further comprise, consist essentially of or consist of reagents for lysis of the cells of the cells or organisms whose viability is being detected in order to release the molecule associated with viability of the one or more cells or organisms. Suitable reagents include by way of example and not limitation phenol, chloroform and proteinase K.

The kits of the invention may further comprise, consist essentially of or consist of one or more nucleases in order to degrade nucleic acid molecules associated with the cells or organisms which provide the molecule associated with viability which is detected in the sample. This may be beneficial to prevent non-specific ligation events for example. This may not be an absolute requirement however, since the nucleic acid molecule and/or further nucleic acid molecules may be designed such that they are not homologous to the nucleic acid molecules of the cell or organism whose viability is being detected. This is discussed in detail above and preferred levels of homology for the nucleic acid molecules of the invention may equally be applied to the nucleic acid molecules included in the kits of the invention.

In one specific embodiment, the kit is provided with suitable buffers that allow all of the components to be provided in the same compartment or storage vessel. Thus, the complete kit is essentially provided as a complete (homogeneous) reaction mix. Thus, the methods of the invention may be carried out in a single reaction step which reduces the possibility of cross contamination of samples and also provides rapid results. Especially preferred is a reaction mix which provides results in real time. Preferably, such a reaction mix is an aqueous composition, but may be provided as a dry powder for reconstitution using sterile or distilled water for example.

Preferably, the reagents included allow an isothermal amplification technique to be utilised, such as TMA. Preferably, the reagents allow the isothermal amplification technique such as TMA to be carried out in real-time.

All kits of the invention may be provided with suitable instructions for use in any one of the methods of the invention. The instructions may be provided as an insert, for example as a booklet provided inside the packaging of the kit and/or may be printed on the packaging of the kit for example.

Thus, according to a still further aspect, the invention provides a spray device for administering the reaction mix which contains all components necessary to carry out the methods of the invention to a surface. Any suitable spray device may be utilised, which may be a pump spray or an aerosolized device for example. Such a device may find application in a number of settings where microbial detection, or detection of any contaminating cells from any source, on a surface is required. For example, where food is being prepared it would be advantageous to be able to ensure that, following cleaning of surfaces after food preparation, no potentially harmful cells or organisms remain on the surface. This ensures that the surface is then "clean" and may be utilised for further food preparation. A kit in which ligases are incorporated is particularly preferred for the spray device of the invention. A spray device can also be used to detect ATP contamination on surfaces in a hygiene monitoring application. Thus, the presence of this molecule associated with viability indicates that some form of contamination is present on the surface, which may be of plant, microbial or animal origin for example. Use of an isothermal DNA amplification method is especially preferred for the detection of a molecule associated with viability, in particular ATP, on a surface. Suitable examples are referred to above in the preferred detection techniques section.

The invention will be further defined by and understood with respect to the accompanying figures and examples in which:

EXAMPLES OF PREFERRED SET UP OF THE ATP DETECTION REACTION REAGENT

Example 1

Figure 2:
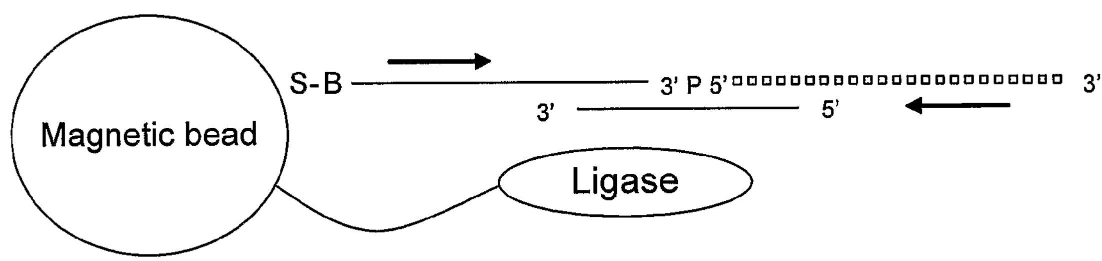
FIG. 2 shows schematically one preferred set up of the reaction reagents for use in the methods of the invention.

In the embodiment shown in FIG. 2, the DNA substrate is supplied to the end-user attached to the magnetic bead covalently or, as shown in the figure, through linkage of the Biotin (B) on the 5' end of the oligo to Streptavidin (S) that has been covalently bound to the bead. In this case the bead is pre-labelled with strepavidin by mixing streptavidin in a suitable molar ratio (determined empirically) with the ligase before linking both covalently to the bead as described previously. In this embodiment the two oligos, with PCR primer sites indicated by arrows, that form the substrate for PCR are linked non-covalently by a third bridging oligo. This 3-oligo structure is stable at room temperature. Upon ligation by ligase in the presence of ATP a stable covalent link is formed between the 3' end of one oligo and the 5' phosphorylated (P) end of the other oligo that then forms the substrate for PCR. In the absence of ligation, no substrate for PCR is formed. The advantage of this format with both the ligase and the DNA substrate bound to the bead is that the ligase is brought into close proximity with the DNA substrate. This enhances the kinetics of the ligation reaction making the detection of ATP more sensitive and also minimises any interference of the ligation from any exogenous DNA eg. bacterial DNA that may be a competing substrate for the ligase.

Exemplary oligos for use according to this example were:

```
                                        SEQ ID NO: 1
5' Biotin
GCCGATATCGGACAACGGCCGAACTGGGAAGGCGCACGGAGAGA 3'

                                        SEQ ID NO: 2
5' Phosphorylated
CCACGAAGTACTAGCTGGCCGTTTGTCACCGACGCCTA 3'

                                        SEQ ID NO: 3
Bridging oligo,
5' TAGTACTTCGTGGTCTCTCCGTGCAA 3' phosphorylated.
```

Example 2

Figure 3:
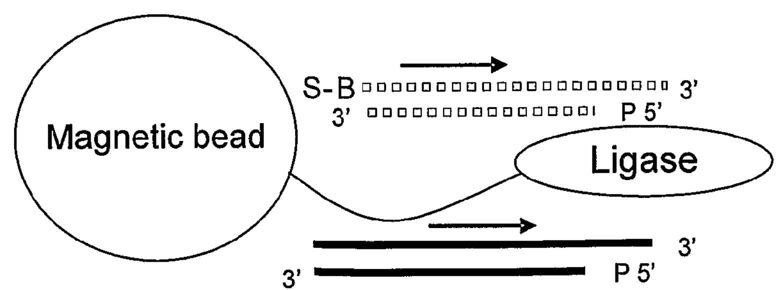
FIG. 3 shows schematically another preferred set up of the reaction reagents for use in the methods of the invention.

In the embodiment shown in FIG. 3 the DNA substrate is supplied to the end-user attached to the magnetic bead covalently or, as shown in the figure, through linkage of the Biotin (B) on the 5' end of the oligos to Streptavidin (S) that has been covalently bound to the bead. In this case the bead is pre-labelled with strepavidin by mixing streptavidin in a suitable molar ratio (determined empirically) with the ligase before linking both covalently to the bead as described previously. In this embodiment the duplex oligos, with PCR primer sites indicated by arrows, that can form the substrate for PCR are both present covalently linked to the bead. Upon ligation by ligase in the presence of ATP a stable covalent link is formed between at least one of the 3' ends of one duplex oligo and the 5' phosphorylated (P) ends of the other duplex oligo. This forms the substrate for PCR. In the absence of ligation, no substrate for PCR is formed. The advantage of this format with both the ligase and the DNA substrate bound to the bead is that the ligase is brought into close proximity with the DNA substrate. This enhances the kinetics of the ligation reaction making the detection of ATP more sensitive and also minimises any interference of the ligation from any exogenous DNA eg. bacterial DNA that may be a competing substrate for the ligase.

Exemplary oligos for use according to this example were:

```
Duplex 1
                                        SEQ ID NO: 4
5' Biotin
GCCGATATCGGACAACGGCCGAACTGGGAAGGCGCACGGAGAGA 3'
```

-continued

```
                                        SEQ ID NO: 5
5' Phosphorylated
CGTGGTCTCTCCGTGCGCCTTCCCAGTTCGGCCGTTGTCCGATAT 3'

Duplex 2
                                        SEQ ID NO: 6
5' Phosphorylated
CCACGAAGTACTAGCTGGCCGTTTGTCACCGACGCCTA 3'

                                        SEQ ID NO: 7
5' Biotin TAGGCGTCGGTGACAAACGGCCAGCTAGTACTT 3'
```

Experiment 1

Demonstration of the Highly Sensitive Detection of ATP Using Ligase

Introduction

Ligase enzyme was coupled to paramagnetic beads and deadenylated. This deadenlyated ligase was used to detect serial dilutions of ATP using a DNA substrate. In the presence of ATP the ligase joined together two pieces of DNA and this new DNA sequence was detected by PCR and agarose gel electrophoresis.

Method

Deadenylation of the ligase and cross-linking of the ligase to the bead 1. 500 µl Dynal M270 amine paramagnetic beads were washed in PBS using a magnet and incubated with 1 mg/ml suberic acid hydroxyl succinate ester (Sigma) in PBS for 30 min at room temperature with shaking.
2. 4000 units of T4 DNA ligase (New England Biolabs) was deadenylated for 30 min at room temperature in 50 mM Hepes pH 7.5, 5 mM sodium pyrophosphate, 10 mM DTT in a volume of 500 µl.
3. The beads were washed ×2 in PBS then in 50 mM. Hepes pH 7.5 and the ligase mix was added to the washed beads and incubated for 30 min at room temperature with shaking.
4. The immobilized ligase was washed ×2 in 50 mM Hepes pH 7.5, 5 mM sodium pyrophosphate, 10 mM DTT and incubated in 500 µl of this wash solution for 10 min.
5. Finally the immobilized ligase was washed ×5 with TBS, 10 mM DTT, 10 mM ethanolamine, 1 mM MgCl2 and stored in 500 µl of this buffer prior to use.

Assay for ATP 1. 25 µl of beads, prepared as described above, were captured and the liquid removed.
2. The beads were resuspended in a 10 µl reaction containing dilutions of ATP in 0.6×TBS, 1 mM MgCl2 and DNA substrate consisting of 10 ng of each of two duplex pieces of DNA with a single stranded complementary overhang and 5' phosphate groups (see FIG. 1). Each DNA duplex was formed by the annealing of the synthetic oligomers in equimolar quantities.

```
                                        SEQ ID NO: 8
5' GCCGATATCGGACAACGCCGAACTGCGAAGGGC 3'

                                        SEQ ID NO: 9
3' CGGCTATAGCCTGTTGCGGCTTGACGCTTCCCGGTTCP 5'

                                        SEQ ID NO: 10
5' PCAAGCGTCATCAGCCGCGTGGCCTTTGTCACCGACGCCTA 3'

                                        SEQ ID NO: 11
3' GCAGTAGTCGGCGCACCGGAAACAGTGGCTGCGGAT 5'
```

3. After 1 hour at room temperature to allow ligation, 5 µl of each reaction was analysed by PCR using standard conditions and the following PCR primers:

```
                                  SEQ ID NO: 12
5' GGACAACGCCGAACTGCGAAGGGC 3'

                                  SEQ ID NO: 13
5' TAGGCGTCGGTGACAAAGGCCACG 3'
```

4. After 25 cycles of PCR the product was analysed by agarose gel electrophoresis on a 3% (w/v) MetaPhor (Cambrex Bio Science) agarose gel.

Results

Figure 1:
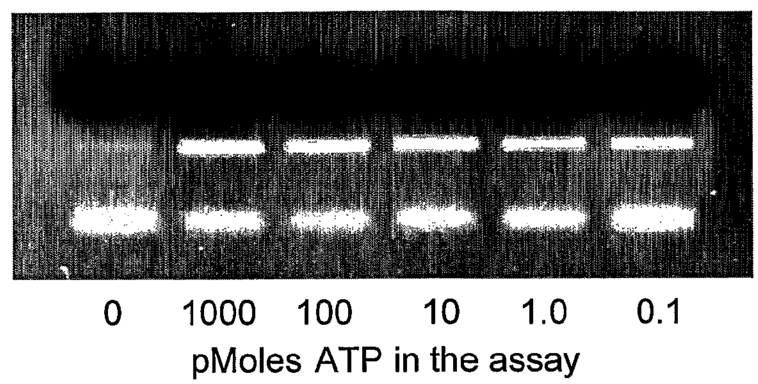
FIG. 1 shows the effectiveness of the methods of the invention. Extremely low concentrations of ATP may be detected according to the methods.

From FIG. 1 it can be seen that very small amounts of ATP present in the ligase reaction could catalyse the ligation or joining of the DNA duplexes to form a new molecule that could be amplified and detected by PCR. From FIG. 1 it can be seen that, in this experiment, as little as 0.1 pmoles of ATP gave a signal that was significantly greater than the signal from the control with no added ATP.

Discussion

This experiment shows that the ligase can be deadenylated and then used as part of a highly sensitive detection method for ATP.

Experiment 2

Demonstration of the Capture of ATP from a Large Volume and Subsequent Highly Sensitive Detection Using Ligase Introduction Ligase enzyme was coupled to a paramagnetic beads and deadenylated as described in experiment 1. This deadenlyated ligase was used to capture ATP which had been diluted into a large volume and the captured ATP was subsequently detected by ligation of a DNA substrate and PCR.

Method

Deadenylation of the bead and cross-linking of the ligase to the bead was as described in Experiment 1.

Assay for ATP 1. 50 µl of ligase-conjugated beads, prepared as described above, were captured and the liquid removed.
2. The beads were resuspended in a 1 ml of TBS, 10 mM DTT, 1 mM $MgCl_2$ containing serial dilutions of ATP and incubated with shaking for 30 min at room temperature. After capture of the ATP, the beads were captured and resuspended in a ligation reaction containing 0.6×TBS, 1 mM MgCl2 and DNA substrate consisting of 10 ng of each of two duplex pieces of DNA as described in experiment 1.
3. After 1 hour at room temperature to allow ligation, 5 µl of each reaction was analysed by PCR and metaphor gel analysis as described in experiment 1.

Results

As little as 0.1 pmoles of ATP diluted into 1 ml of TBS gave a signal that was significantly greater than the signal from the control with no added ATP.

Discussion

This experiment shows that the deadenylated ligase can capture small amounts of ATP from a large volume which can then be detected using ligation and PCR analysis of the ligated product. This demonstrates that the invention can be used to concentrate ATP prior to testing.

Experiment 3

Limits of Detection of ATP

Method

1. Ten-fold dilutions of ATP were prepared in 100 µl of ligase buffer (50 mM Tris pH 7.5, 1 mM MgCl2, 1 mM DTT).
2. 5 µl ligase/DNA substrate paramagnetic beads (prepared as described in FIG. 3, see above) were added and incubated at 8° C. for 60 min.
3. The beads were then collected using a magnet and resuspended in 20 µl ligase buffer.
4. After heating at 95° C. for 5 min, 2 µl of the eluted ligated product was quantitated by PCR.
5. The PCR was performed on a quantitative PCR machine, PTC-200, GRI using the following primers:

```
                                  SEQ ID NO: 14
5' GGACAACGGCCGAACTGGGAAGGC 3'

Figure 4:
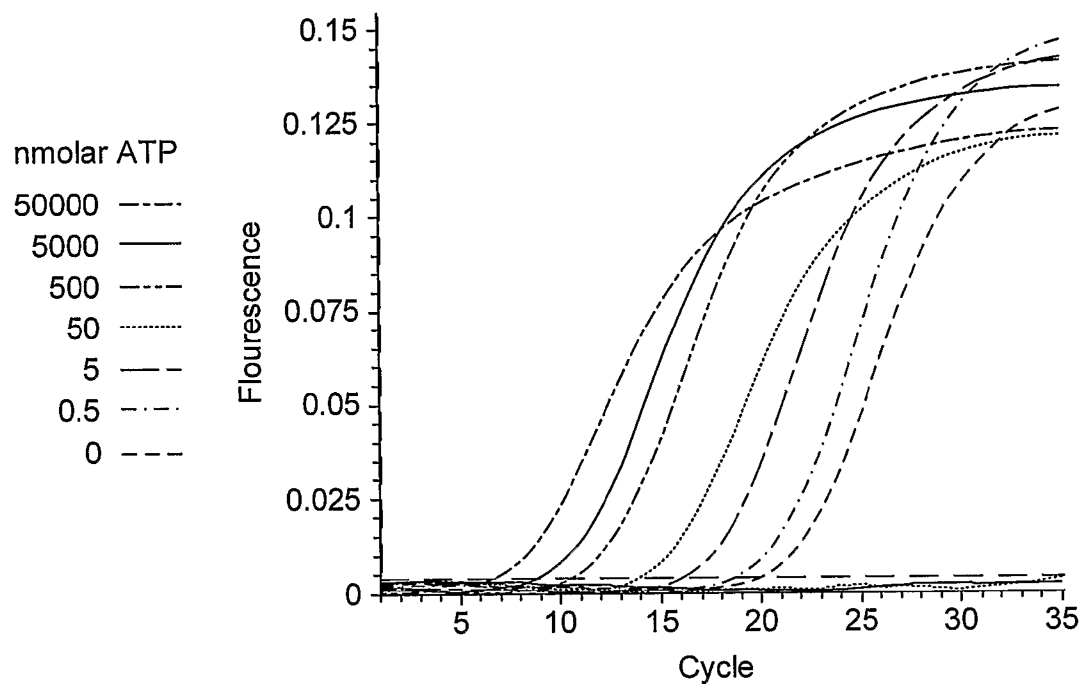
FIG. 4 presents the real time PCR measurements of ATP-dependent ligase-mediated covalent linking of DNA strands. The results of using various ATP levels in the reactions are shown as separate curves on the same graph. Fluorescence read out is plotted against cycle number.

SEQ ID NO: 15
5' TAG GCGTCGGTGACAAACGGCCAGC 3'
``` under standard conditions using the qPCR Mastermix SYBR Green 1—No Rox PCR mix from eurogentec. The cycles were 2 min 50° C., 15 min 95° C. then 40 cycles of 95° C. for 10 sec, 65° C. for 15 sec and 72° C. for 15 sec. The fluorescence of SYBR green dye was measured at the end of each 72° C. step (see FIG. 4).

Results

The graph shows the real time measure of the ATP-dependent ligase-mediated covalent linking of DNA strands that are then detected by PCR. As more ATP is present in the reaction there is more ligation of the DNA strands and more DNA is detected by PCR.

Discussion

As expected, as the concentration of ATP increased there was a correlated increase in ligated DNA product, as measured by the quantitative PCR, all of which were greater than that observed in the zero ATP control.

Experiment 4

Demonstration of the Detection of ATP within Growing Bacteria

Method

1. A bacterial culture of *E. coli* was prepared in LB media and grown to stationary phase at 37° C. overnight.
2. The following day, ten-fold dilutions of the bacterial culture were prepared in LB media and grown for 3 hours at 37° C.
3. After incubation, a suitable dilution of the bacteria were quantitated by plating out on LB agar plates, incubating overnight and counting the number of colonies.
4. For the quantitaion of ATP, 10 µl of each 3 hour culture were added to 2.5 µl of 1M NaOH, 1% (v/v) Triton X-100 and incubated for 5 min before neutralisation with 25 µl of 0.1M HCL.
5. 100 µl of ligase buffer was then added followed by 5 µl ligase/DNA substrate paramagnetic beads (prepared as described in Example 1 above).
6. After incubation at 8° C. for 60 min, the beads were collected using a magnet and resuspended in 20 µl ligase buffer.
7. After heating at 95° C. for 5 min, 2 µl of the eluted ligated product was quantitated by PCR.
8. The quantitative PCR was performed as described previously.

Results

Figure 5:
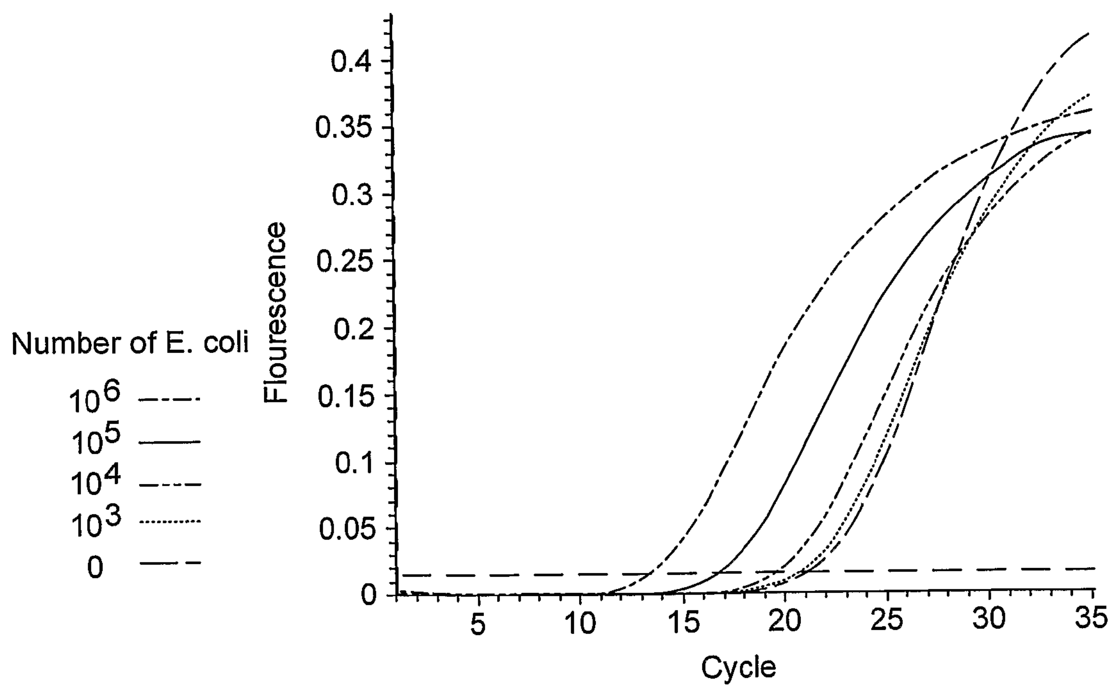
FIG. 5 shows the signal from the quantitative PCR as a measure of ATP catalysed covalent linking of the DNA substrate for varying numbers of bacteria in the ATP assay as determined by plate counts.

The signal from the quantitative PCR as a measure of ATP catalysed covalent linking of the DNA substrate declined in accordance with the decline of the number of bacteria in the ATP assay as determined by plate counts (see FIG. 5). It was determined that the ATP contained within $10^6$-$10^4$ bacteria gave a signal in the quatitative PCR which was greater than the no-ATP control.

Discussion

The ATP assay involving ATP-dependent ligase joining of DNA strands could detect the amount of ATP contained within $10^4$ *E. coli.*

Experiment 5

Demonstration of the Susceptibility of Bacteria to Antibiotic Using the ATP Assay Method 1. A bacterial culture of a tetracycline sensitive strain of *E. coli* was prepared in LB media and grown to stationary phase at 37° C. overnight.
2. The following day, a hundred-fold dilution of the bacterial culture were prepared in LB media with and without tetracycline and grown for 3 hours at 37° C.
3. For the quantitation of ATP, 10 µl of each 3 hour culture were added to 2.5 µl of 1M NaOH, 1% (v/v) Triton X-100 and incubated for 5 min before neutralisation with 25 µl of 0.1M HCL.
4. 100 µl of ligase buffer was then added followed by 5 µl ligase/DNA substrate paramagnetic beads (prepared as described in Example 1 above).
5. After incubation at 8° C. for 60 min, the beads were collected using a magnet and resuspended in 20 µl ligase buffer.
6. After heating at 95° C. for 5 min, 2 µl; of the eluted ligated product was quantitated by PCR.
7. The quantitative PCR was performed as described previously.

Results

Figure 6:
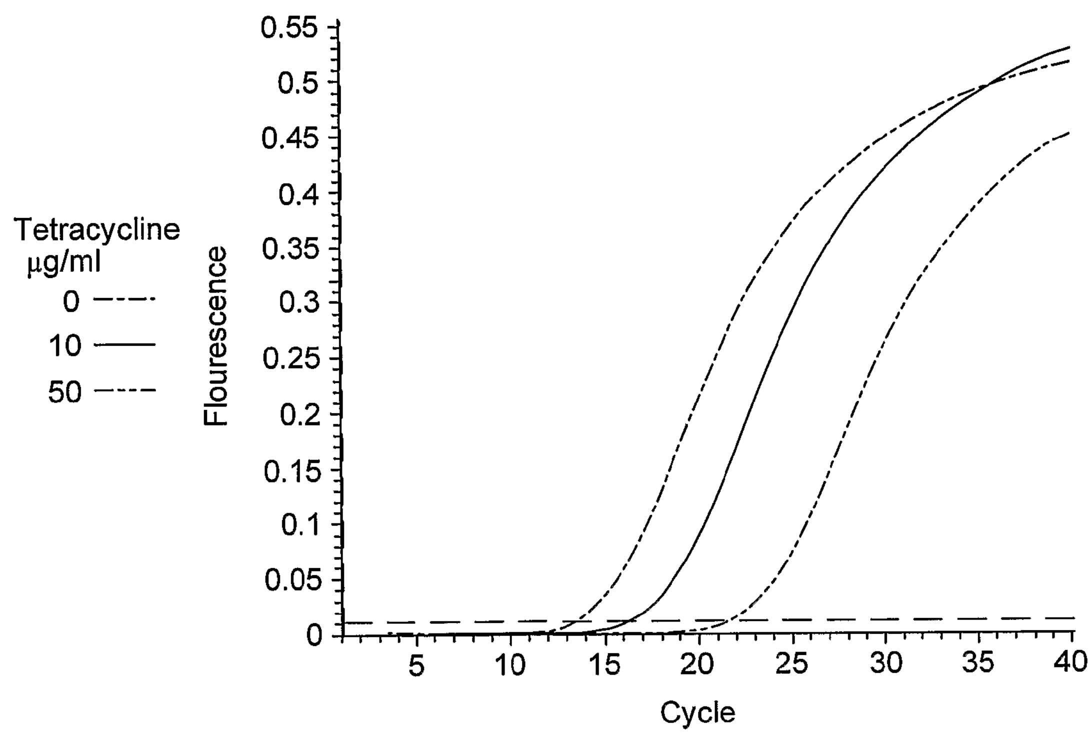
FIG. 6 shows results of quantitative PCR representing the amount of ATP-catalysed ligation of the DNA substrate strands dependent upon the amount of tetracycline in the growth media.

From the quantitative PCR (FIG. 6) it can be seen that the amount of ATP-catalysed ligation of the DNA substrate strands declines with increasing amounts of tetracycline in the growth media. This reflects the fact that as this *E. coli* strain is susceptible to tetracycline its growth in the presence of the antibiotic is restricted and the bacteria decrease in viability. This in turn leads to less ATP in the bacteria and, when released from the bacteria and measured, less ATP dependent ligation of the DNA substrate in our assay. The decreased formation of covalently ligated DNA product is reflected in a delayed quantitative PCR signal.

Discussion

The susceptibility of bacteria to antibiotic can clearly be demonstrated by this novel ATP assay, in which antibiotic treatment causes a loss of viability of the bacteria with a concomitant decrease in the amount of ATP measured.

Experiment 6

Demonstration of the Susceptibility of *Staphylococcus aureus* Bacteria to Antibiotic Using the ATP Assay Method 1. A bacterial culture of a clinical isolate of a MRSA and antibiotic sensitive strain of *Staphylococcus aureus* strain were prepared in Nutrient media (Lab M, UK) and grown to stationary phase at 37° C. overnight.
2. The following day, a hundred-fold dilution of the bacterial cultures were prepared in the same media with 1 µl alkaline phosphatase (10 units, New England Biolabs) with and without 60 µg/ml oxacillin and grown for 3 hours at 37° C.
3. For the quantitation of ATP, 10 µl of each 0 (10 µl culture removed and treated at time 0 min) and 3 hour culture were added to 2.5 µl of 1M NaOH, 1% (v/v) Triton X-100 and incubated for 5 min before neutralisation with 25 µl of 0.1M HCL.
4. 100 µl of ligase buffer was then added followed by 5 µl ligase/DNA substrate paramagnetic beads (prepared as described in Example 2 above).
5. After incubation at 8° C. for 60 min, the beads were collected using a magnet and resuspended in 20 µl ligase buffer.
6. After heating at 95° C. for 5 min, 2 µl of the eluted ligated product was quantitated by PCR.
7. The quantitative PCR was performed as described previously.

Results

Figure 7:
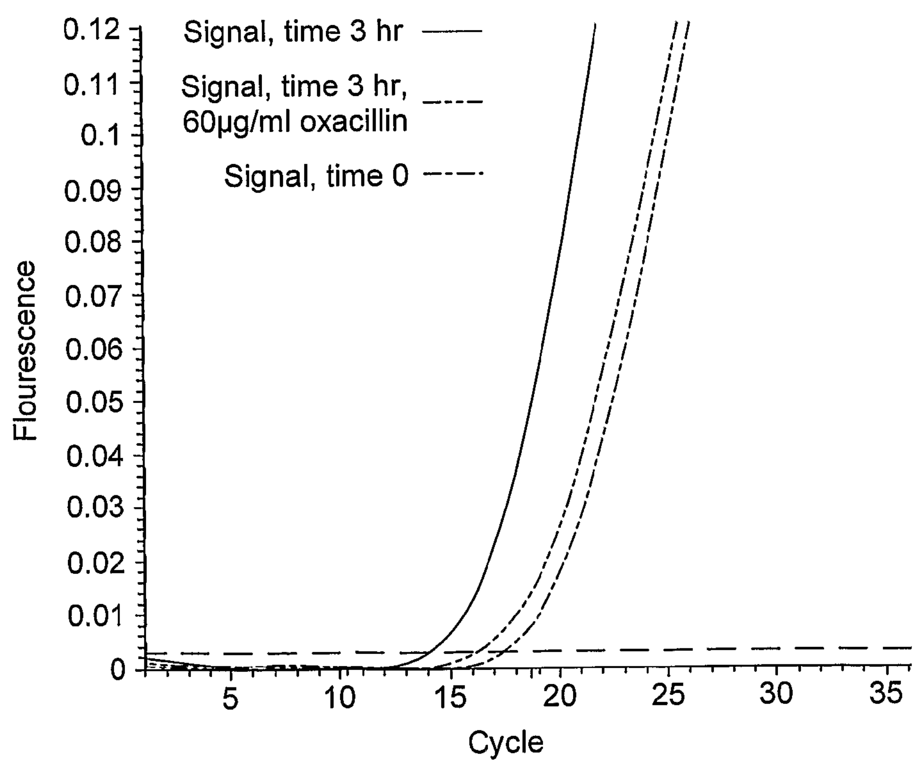
FIG. 7 shows the real-time quantitative PCR results for ATP production by a methicillin sensitive strain that shows no resistance to a challenge with oxacillin.

FIG. 7 shows the results for a methicillin sensitive strain that shows no resistance to the challenge antibiotic of oxacillin (an in vitro antibiotic used as a surrogate for methicillin). There is growth and an increase of ATP observed after 3 hr compared to the zero time point. This growth and increase in ATP is not observed when the organism is grown in the presence of oxacillin. The organism is sensitive to this antibiotic and the decreased viability of the organism is shown by the decrease in ATP in the organism.

Figure 8:
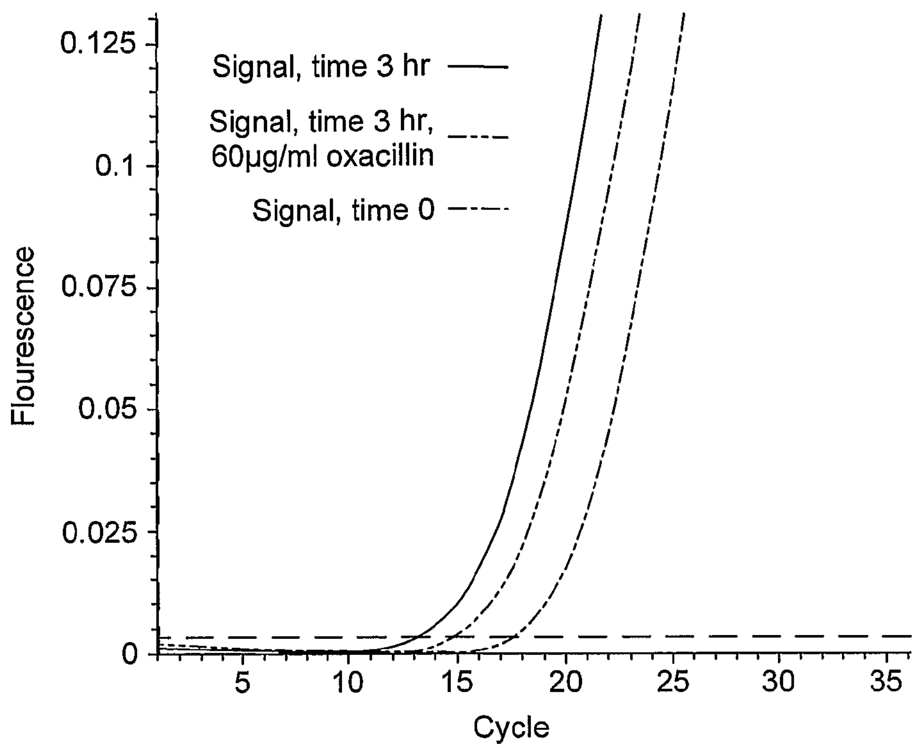
FIG. 8 shows the real-time quantitative PCR results for a methicillin resistant strain that shows resistance to a challenge with oxacillin.

FIG. 8 shows the results for a methicillin resistant strain that shows resistance to the challenge antibiotic of oxacillin (an in vitro antibiotic used as a surrogate for methicillin). There is growth and an increase of ATP observed after 3 hr in the absence of antibiotic compared to the zero time point. This growth and increase in ATP is reduced but not abrogated when the organism is grown in the presence of 60 µg/ml oxacillin. The organism is not sensitive to this antibiotic and continues to grow and produce ATP in the presence of this antibiotic.

Discussion

There is a clear difference in the ATP content of the MRSA and sensitive clinical isolates of *Staphylococcus aureus* after growth in the presence of oxacillin. The sensitive strain of bacteria loses viability and ATP when grown in this antibiotic whereas the resistant MRSA strain continues to remain viable and maintains a higher level of ATP.

Experiment 7

Investigation of the Effect of Removing Exogenous ATP by Alkaline Phosphatase

Method

1. A bacterial culture of a clinical isolate of a *Staphylococcus aureus* strain was prepared in Nutrient media (Lab M, UK) and grown to stationary phase at 37° C. overnight.
2. The following day, a hundred-fold dilution of the bacterial cultures were prepared in the same media with and without 1 µl alkaline phosphatase (10 units, New England Biolabs) and grown for 3 hours at 37° C.
3. For the quantitation of ATP, 10 µl of each 0 (10 µl culture removed and treated at time 0 min) and 3 hour culture were added to 2.5 µl of 1M NaOH, 1% (v/v) Triton X-100 and incubated for 5 min before neutralisation with 25 µl of 0.1M HCL.
4. 100 µl of ligase buffer was then added followed by 5 µl ligase/DNA substrate paramagnetic beads (prepared as described in Example 2 above).

5. After incubation at 8° C. for 60 min, the beads were collected using a magnet and resuspended in 20 μl ligase buffer.
6. After heating at 95° C. for 5 min, 2 μl of the eluted ligated product was quantitated by PCR.
7. The quantitative PCR was performed as described previously.

Results

Figure 9:
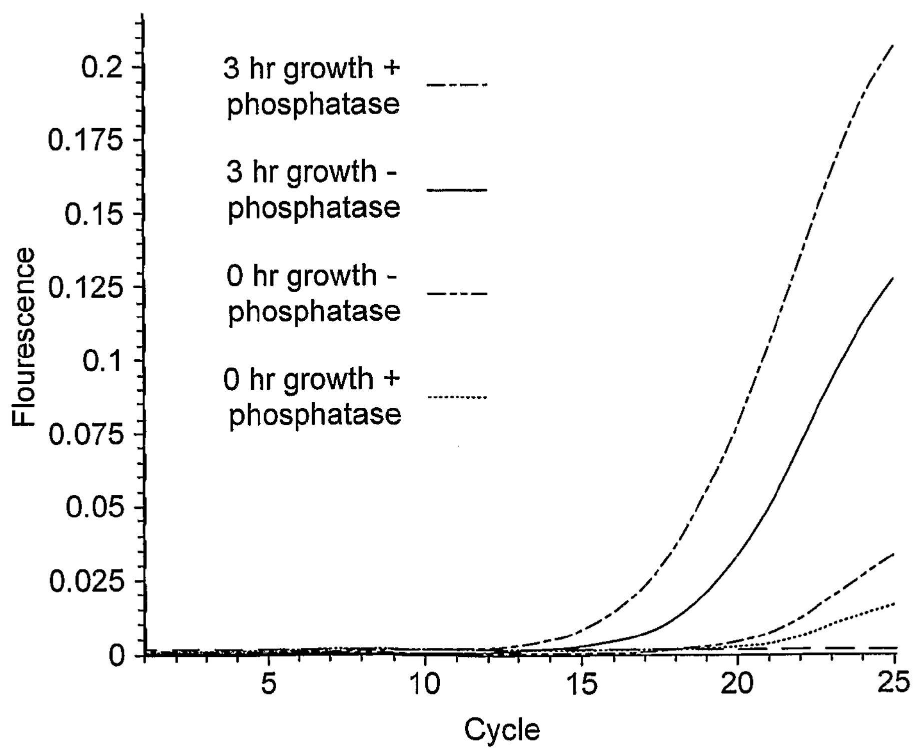
FIG. 9 shows the effect of removing exogenous ATP through inclusion of alkaline phosphatase in the experiments.

The alkaline phosphatase results in a decreased signal for the zero time point (see FIG. 9). Presumably this is because any ATP that has accumulated in the media from the growing cells has been removed and is not detected in this assay. Less obviously, the inclusion of phosphatase in the media during cell growth increases the signal at 3 hr compared to the no phosphatase control. The reasons for this are unclear.

Discussion

The inclusion of ATP degrading enzymes or agents such as alkaline phosphatase during cell growth helps remove any ATP released from non-viable or dying leaky cells and gives a much better differential signal between the zero control and cells that have had a phase of growth.

All references cited herein are hereby incorporated specifically as part of the present disclosure.

The invention claimed is:

1. A method of detecting a molecule associated with viability of one or more cells or organisms in a sample, comprising the steps of:

a) contacting the sample with a ligase, which ligase is capable of adding a chemical moiety to a nucleic acid molecule only in the presence of the molecule associated with viability of the one or more cells or organisms, thereby generating a novel detectable nucleic acid molecule; and b) detecting the presence of the molecule associated with viability of the one or more cells or organisms by detecting the novel nucleic acid molecule generated only in the presence of the molecule associated with viability of the one or more cells or organisms.

2. The method according to claim 1 wherein the novel nucleic acid molecule is generated by ligation of the nucleic acid molecule with a further nucleic acid molecule.

3. The method according to claim 1 wherein the ligase comprises T4 DNA ligase or T4 RNA ligase.

4. The method according to claim 1 wherein the molecule associated with viability of the one or more cells or organisms comprises ATP.

5. The method according to claim 1 wherein the ligase comprises *E. coli* DNA ligase.

6. The method according to claim 5 wherein the molecule associated with viability of the one or more cells or organisms comprises NAD+.

7. The method according to claim 1 wherein the one or more cells or organisms comprises bacteria and/or yeast.

8. The method according to claim 1 wherein the novel nucleic acid molecule is detected using nucleic acid amplification techniques.

9. The method according to claim 1 which comprises, prior to step (a), filtering the sample to concentrate the one or more cells or organisms.

10. The method according to claim 1 which further comprises, prior to step (a), lysing other cells in the sample, but not those of the one or more cells or organisms to be detected.

11. The method according to claim 1 which further comprises removing or exhausting from the sample any molecules associated with viability of the one or more cells or organisms which are not provided by the one or more cells or organisms.

12. The method according to claim 1 which further comprises lysing the cells of the one or more cells or organisms in order to release the molecule associated with viability of the one or more cells or organisms.

13. The method according to claim 1 which further comprises treatment of the sample with one or more nucleases in order to degrade nucleic acid molecules associated with the one or more cells or organisms.

14. The method according to claim 1 wherein the enzyme and/or nucleic acid molecule and/or further nucleic acid molecule is immobilized on a solid support.

15. A method of screening for:

(i) resistance of a cell or organism to a molecule directed against said cell or organism, and/or (ii) molecules which are capable of killing a cell or organism, the method comprising:

(a) exposing the cell or organism to the molecule; and (b) carrying out the method as defined in claim 1, wherein if there is resistance to the molecule and/or if the molecule is capable of killing the cell or organism, the novel nucleic acid molecule will be detected.

16. A method of monitoring growth of a cell culture the method comprising:

(a) carrying out the method as defined in claim 1, and (b) determining the presence and/or levels of the novel nucleic acid molecule in order to determine the growth of the cell culture.

17. A method of diagnosing an infection, or a disease associated with the presence of a viable cell or organism in a subject, comprising, in a sample obtained from the subject:

(a) selecting from the sample the cell or organism whose viability is to be detected;

(b) contacting the sample with ligase, which ligase is capable of adding a chemical moiety to a nucleic acid molecule in the presence of a molecule associated with viability of the cell or organism, thereby generating a novel detectable nucleic acid molecule; and (c) detecting the presence of the viable cell or organism by detecting the novel nucleic acid molecule generated only in the presence of the molecule associated with viability of the cell or organism, wherein if the novel nucleic acid molecule is detected the subject is considered to be infected, or to have the disease.

18. A method of determining the toxicity of a candidate pharmaceutical agent or agricultural agent to mammalian or plant cells comprising the steps of, in a sample of mammalian or plant cells:

(a) exposing the cells to the agent;

(b) contacting the sample with ligase, which ligase is capable of adding a chemical moiety to a nucleic acid molecule in the presence of a molecule associated with viability of the cells, thereby generating a novel detectable nucleic acid molecule; and (c) detecting whether the molecule is toxic to the cells by detecting the novel nucleic acid molecule generated only in the presence of the molecule associated with viability of the cells;

wherein if the molecule is toxic to the cells, the novel nucleic acid molecule will not be detected.

19. The method according to claim 1 wherein the sample volume is between 1 and 5 ml.

* * * * *

SEQUENCE LISTING

```
<160> NUMBER OF SEQ ID NOS: 15

<210> SEQ ID NO 1
<211> LENGTH: 44
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(44)

<400> SEQUENCE: 1

gccgatatcg gacaacggcc gaactgggaa ggcgcacgga gaga                 44


<210> SEQ ID NO 2
<211> LENGTH: 38
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(38)

<400> SEQUENCE: 2

ccacgaagta ctagctggcc gtttgtcacc gacgccta                        38


<210> SEQ ID NO 3
<211> LENGTH: 26
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(26)

<400> SEQUENCE: 3

tagtacttcg tggtctctcc gtgcaa                                     26


<210> SEQ ID NO 4
<211> LENGTH: 44
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (3)..(44)

<400> SEQUENCE: 4

gccgatatcg gacaacggcc gaactgggaa ggcgcacgga gaga                 44
```

<210> SEQ ID NO 5
<211> LENGTH: 45
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (3)..(45)

<400> SEQUENCE: 5
cgtggtctct ccgtgcgcct tcccagttcg gccgttgtcc gatat 45

<210> SEQ ID NO 6
<211> LENGTH: 38
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(38)

<400> SEQUENCE: 6
ccacgaagta ctagctggcc gtttgtcacc gacgccta 38

<210> SEQ ID NO 7
<211> LENGTH: 33
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (3)..(33)

<400> SEQUENCE: 7
taggcgtcgg tgacaaacgg ccagctagta ctt 33

<210> SEQ ID NO 8
<211> LENGTH: 33
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(33)

<400> SEQUENCE: 8
gccgatatcg gacaacgccg aactgcgaag ggc 33

<210> SEQ ID NO 9
<211> LENGTH: 37
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (3)..(37)

<400> SEQUENCE: 9
cggctatagc ctgttgcggc ttgacgcttc ccggttc 37

<210> SEQ ID NO 10
<211> LENGTH: 40
<212> TYPE: DNA
<213> ORGANISM: Artificial

```
<220> FEATURE:
<223> OTHER INFORMATION: oligonucleotide
<220> FEATURE:
<221> NAME/KEY: misc_feature
<222> LOCATION: (1)..(40)

<400> SEQUENCE: 10

caagcgtcat cagccgcgtg gcctttgtca ccgacgccta                    40


<210> SEQ ID NO 11
<211> LENGTH: 36
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(36)

<400> SEQUENCE: 11

gcagtagtcg gcgcaccgga aacagtggct gcggat                        36


<210> SEQ ID NO 12
<211> LENGTH: 24
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(24)

<400> SEQUENCE: 12

ggacaacgcc gaactgcgaa gggc                                     24


<210> SEQ ID NO 13
<211> LENGTH: 24
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(24)

<400> SEQUENCE: 13

taggcgtcgg tgacaaaggc cacg                                     24


<210> SEQ ID NO 14
<211> LENGTH: 24
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(24)

<400> SEQUENCE: 14

ggacaacggc cgaactggga aggc                                     24


<210> SEQ ID NO 15
<211> LENGTH: 25
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (1)..(25)
```

<400> SEQUENCE: 15
taggcgtcgg tgacaaacgg ccagc 25